(12) United States Patent
Gu et al.

(10) Patent No.: US 8,716,502 B2
(45) Date of Patent: May 6, 2014

(54) PROCESS FOR PREPARING DIVINYLARENE OXIDES

(75) Inventors: Leming Gu, Lake Jackson, TX (US); William W. Fan, Lake Jackson, TX (US); David Jean, Friendswood, TX (US); Eric B. Ripplinger, Lake Jackson, TX (US); Bruce D. Hook, Lake Jackson, TX (US); David H. West, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/990,451

(22) PCT Filed: Dec. 7, 2011

(86) PCT No.: PCT/US2011/063677
§ 371 (c)(1), (2), (4) Date: May 30, 2013

(87) PCT Pub. No.: WO2012/082482
PCT Pub. Date: Jun. 21, 2012

(65) Prior Publication Data
US 2013/0267720 A1  Oct. 10, 2013

Related U.S. Application Data

(60) Provisional application No. 61/424,322, filed on Dec. 17, 2010.

(51) Int. Cl.
*C07D 301/03* (2006.01)
*C07D 301/12* (2006.01)

(52) U.S. Cl.
USPC .......................................... 549/531; 549/523

(58) Field of Classification Search
USPC ................................................. 549/523, 531
See application file for complete search history.

(56) References Cited

U.S. PATENT DOCUMENTS

| | | | |
|---|---|---|---|
| 2,388,235 A | 7/1941 | Bowman et al. | |
| 2,591,573 A | 7/1947 | McBurney | |
| 2,912,389 A | 11/1959 | Phillips et al. | |
| 2,977,374 A | 3/1961 | Phillips et al. | |
| 3,053,856 A * | 9/1962 | Payne et al. ................... | 549/526 |

FOREIGN PATENT DOCUMENTS

FR  2419938  10/1979

OTHER PUBLICATIONS

Worzakowska, Influence of Cure Schedule on the Viscoelastic Properties and Thermal Degraddation of Crosslinked Monoand Diepoxides Obtained from During the Reaction of Hydrogen Peroxide and Divinyl benzene,2006, Journal of Applied Polymer Science, vol. 103, No. 1, p. 462-469.*
M. Worzakowska, J Appl. Poly. Sci., 2007, vol. 103, pp. 462-469.
Payne et al., J Org. Chem., 1961, vol. 26, p. 659.
K. Kaneda et al., Chem. Commun., 1998, pp. 295-296.

* cited by examiner

*Primary Examiner* — T. Victor Oh

(57) ABSTRACT

A process for preparing a divinylarene oxide including (a) reacting (i) at least one divinylarene; (ii) at least one peroxycarboximidic acid; (iii) at least one solvent; and (iv) at least one basic compound, under reaction conditions to form a reaction effluent containing a divinylarene oxide product; and then (b) evaporating the reaction effluent of step (a) to form a concentrate containing the divinylarene oxide product; and wherein the concentrate separates into two liquid phases.

16 Claims, 2 Drawing Sheets

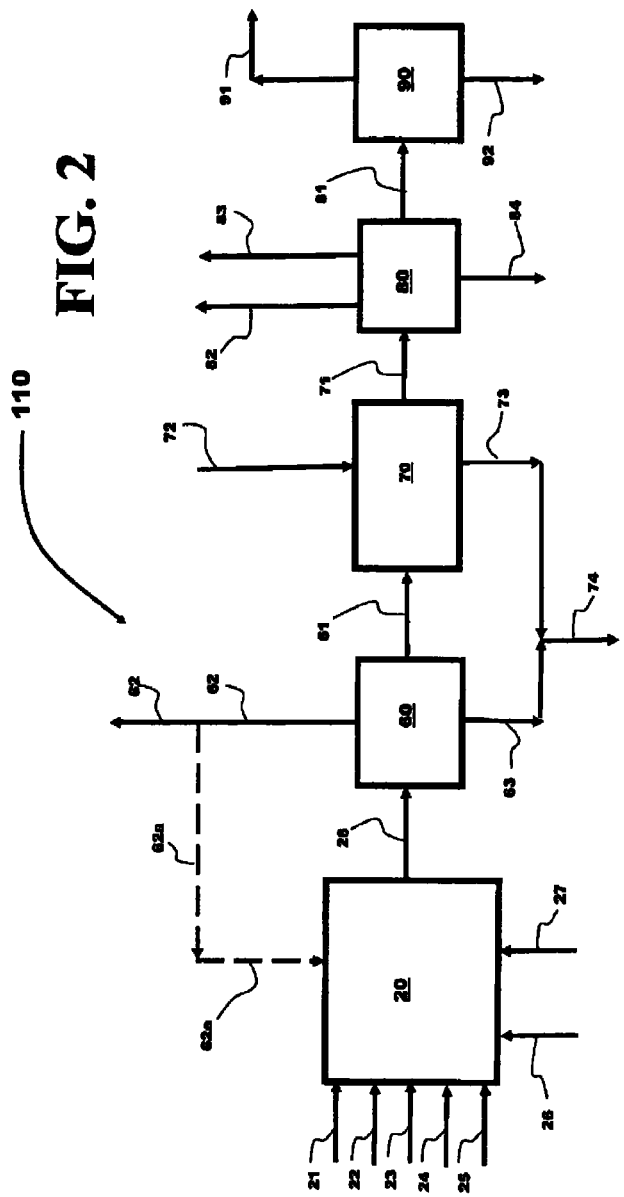

PROCESS FOR PREPARING DIVINYLARENE OXIDES

BACKGROUND OF THE INVENTION

1. Field of the Invention

The present invention is related to a process for preparing divinylarene oxides, particularly divinylarene dioxides derived from divinylarene. More specifically, the present invention relates to a process for preparing a divinylarene oxide including reacting (a) at least one divinylarene; and (b) at least one peroxycarboximidic acid.

2. Description of Background and Related Art

In general, epoxidation of olefins can be accomplished by a variety of different methods. For instance, the prior art methods include: (1) reaction of an olefin with hypochlorite to form a chlorohydrin, followed by reaction with a base to form an epoxide; (2) oxidation by peroxy carboxylic acids; (3) oxidation by organic hydroperoxides with a catalyst; (4) oxidation by hydrogen peroxide with a catalyst; or (5) oxidation by other oxidants such as sodium hypochlorite, iodosyl benzene, or peroxycarbonate in the presence of a catalyst.

Epoxidation of olefins by peroxycarboximidic acids is disclosed in U.S. Pat. No. 3,053,856. In the process of U.S. Pat. No. 3,053,856, hydrogen peroxide reacts with a nitrile under controlled pH conditions to form a peroxycarboximidic acid which reacts with an olefin to form an epoxide and an amide. The overall reaction is shown below with acetonitrile and hydrogen peroxide used to make the peroxyacetimidic acid:

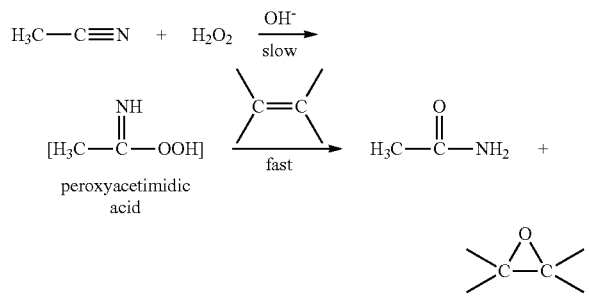

M. Worzakowska, *J. Appl. Poly. Sci.*, 2007, Vol. 103, pp. 462-469, discloses epoxidizing divinylbenzene (DVB) by a method similar to that described in U.S. Pat. No. 3,053,856 using acetonitrile-hydrogen peroxide with magnesium oxide catalyst and greater than a 4 fold molar excess of hydrogen peroxide to olefin. Worzakowska reports a 90 percent (%) degree of epoxidation. In the method of Worzakowska, DVB, acetonitrile, water (pH 10), and MgO are charged into a reactor, warmed to 50° C., whereupon addition of a mixture of 60% hydrogen peroxide and methanol are added slowly over 2 hours, followed by continued heating and stirring for a total of 5 hours. The method used by Worzakowska is disadvantaged in terms of process safety and economics due to the large excess of hydrogen peroxide required. This excess of hydrogen peroxide has to be recovered and reused for Worzakowska's method to be viable on an industrial scale.

U.S. Pat. No. 2,977,374 discloses epoxidizing DVB using peracetic acid in ethyl acetate and reports a divinylbenzene dioxide (DVBDO) yield of 49%. In U.S. Pat. No. 2,977,374, an 81% yield of styrene oxide is reported. Although olefins such as styrene and DVB are structurally similar, epoxidation of these two olefins will not necessarily give comparable results, as shown in U.S. Pat. No. 2,977,374. Epoxidation using peracetic acid generates acetic acid as a co-product which is known to react with the epoxide product to give a hydroxy ester byproduct, thereby lowering the yield of the epoxide product. In the case of a diolefin, there is twice as great a probability that any given molecule of starting diolefin will form a byproduct as compared to the corresponding monoolefin.

Payne et al., *J. Org. Chem.*, 1961, Vol. 26, p. 659 discloses generally the use of hydrogen peroxide for alkali catalyzed epoxidation and oxidation using a nitrile as a co-reactant. In the above Payne et al. reference, various epoxide products are generally recovered by chloroform extractions.

French Patent No. 2419938 discloses an example of distillation at 140 mmHg and 27~28° C., to separate styrene oxide (an organic layer) from an aqueous phase by removing methanol and acetonitrile. French Patent No. 2419938 does not disclose a process for manufacturing a divinylarene dioxide.

U.S. Pat. No. 2,912,389 discloses recovering DVBDO via fractional distillation from inert solvents, such as acetone or ethyl acetate. U.S. Pat. No. 2,912,389 does not disclose a process which produces a biphasic material produced during the process of preparing a divinylarene dioxide.

In view of the problems with the known prior art processes, it is desired to provide a process to make a divinylarene oxide, particularly a divinylarene dioxide such as DVBDO, on an industrial scale which gives good yields of divinylarene dioxide product at the lowest possible oxidant cost.

SUMMARY OF THE INVENTION

The present invention is directed to a process for manufacturing at least one divinylarene oxide including the steps of:

(a) reacting (i) at least one divinylarene with (ii) at least one peroxycarboximidic acid epoxidizing agent in the presence of (iii) at least one solvent and (iv) at least one basic compound to form a reaction effluent comprising at least one divinylarene oxide and at least one amide;

(b) removing at least a portion of the at least one solvent from the reaction effluent of step (a) forming a biphasic concentrate comprising (b1) an organic phase containing at least a portion of the at least one divinylarene oxide and (b2) an aqueous phase; and (c) separating the organic phase containing the at least one divinylarene oxide from the aqueous phase.

In one embodiment, step (b) of the process of the present invention includes:

(b) evaporating the reaction effluent of step (a) to remove "lights" (defined herein below) from the at least one divinylarene oxide; wherein a biphasic liquid concentrate is formed without the addition of any additional organic solvent; and wherein the biphasic liquid concentrate separates into (b1) an organic phase and (b2) an aqueous phase; said organic phase containing at least a portion of the at least one divinylarene oxide product.

In another embodiment of the present invention, the process includes separating a crude divinylarene oxide such as a crude DVBDO product from a reaction mixture after synthesis by, for example, vacuum stripping off "lights". In this embodiment, the remaining mixture separates autonomously to a divinylarene oxide-rich (e.g. a DVBDO-rich) oil layer and an aqueous layer. This provides the benefit of eliminating the use of an extracting solvent, therefore reducing water and solvent usage in the overall process.

In still another embodiment, the present invention includes a process of separating, for example by vacuum distillation, of lighter solvent (for example methanol, acetonitrile) from the reaction effluent to specifically form a product (e.g., DVBDO) rich organic phase and a by-product rich aqueous phase, followed by phase separation and recovery. The combination of steps in the present invention reduces the amount of process solvent and water used. In addition, a halogenated solvent may not have to be used which results in less contamination of the resultant desired product.

BRIEF DESCRIPTION OF THE DRAWINGS

For the purpose of illustrating the present invention, the following drawings show a form of the present invention which is presently preferred. However, it should be understood that the present invention is not limited to the precise arrangements and apparatuses shown in the drawings. In the accompanying drawings, like reference numerals are used to denote like parts throughout the several drawings.

FIG. 2 is a block flow diagram showing one embodiment of the process of the present invention carried out with a stripping step.

DETAILED DESCRIPTION OF THE INVENTION

Figure 1:
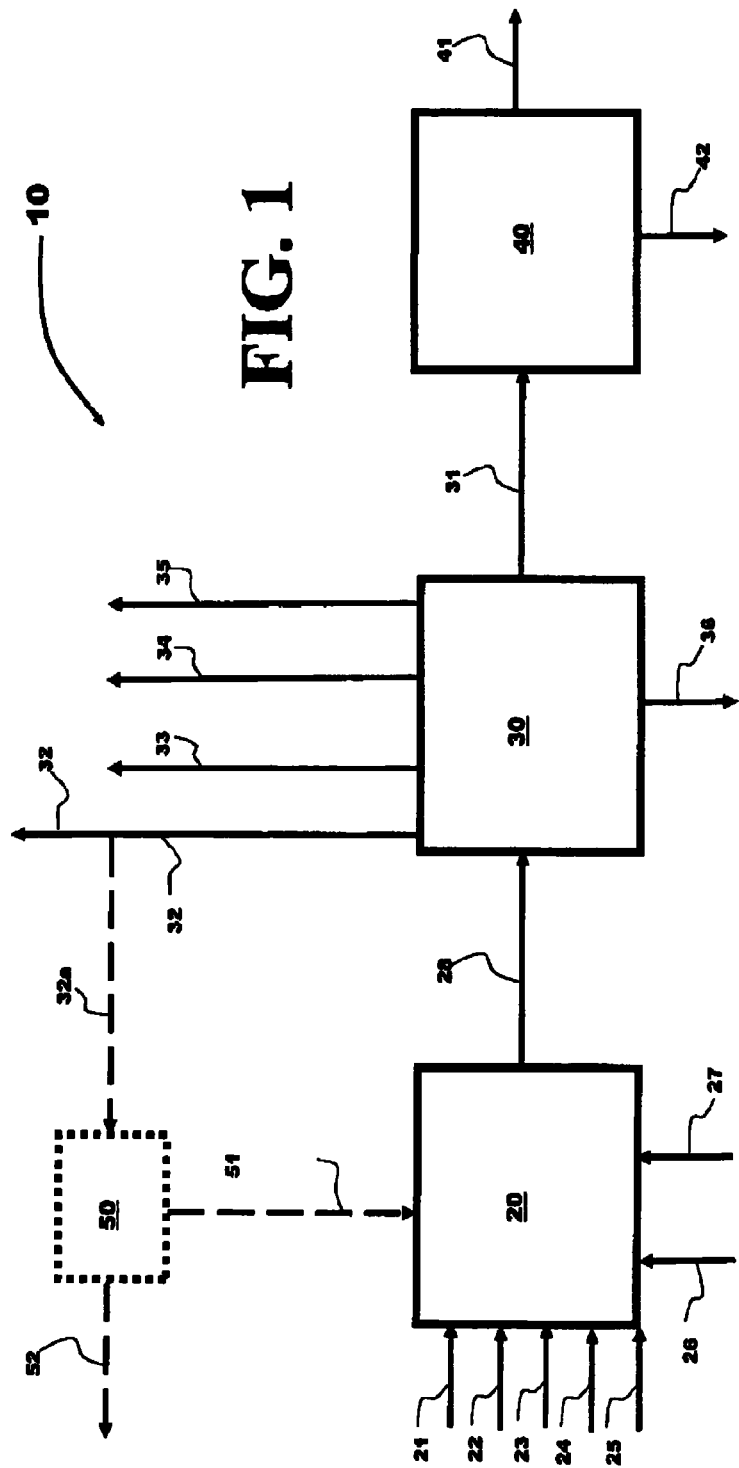
FIG. 1 is a block flow diagram showing a process carried out without a stripping step.

"Divinylarene oxide" herein means at least one of monoxides, dioxides, polyfunctional oxides, and mixtures thereof.

"Lights" herein means components that have a boiling point of lower than 200° C. at atmospheric pressure. The lights may be present at various points of the process of the present invention for example during the evaporation operation of this invention as described herein. The lights of this invention may include components such as for example, but not limited to, divinylarene, methanol, water, acetonitrile, or mixtures thereof.

In its broadest scope the present invention includes a process for manufacturing at least one divinylarene oxide comprising the steps of:

(a) reacting (i) at least one divinylarene with (ii) at least one peroxycarboximidic acid epoxidizing agent in the presence of (iii) at least one solvent and (iv) at least one basic compound, to form a reaction effluent comprising at least one divinylarene oxide and at least one amide;

(b) removing at least a portion of at least one lights present in the reaction effluent of step (a) from the reaction effluent of step (a) forming a biphasic liquid concentrate comprising (b1) an organic phase containing at least a portion of the at least one divinylarene oxide and (b2) an aqueous phase; and (c) separating the organic phase containing the at least one divinylarene oxide from the aqueous phase.

The first reaction step (a) of the above process of the present invention includes an epoxidation reaction step comprising reacting components (i)-(iv) under conditions to form a reaction effluent comprising at least one divinylarene oxide.

The source of divinylarene useful in the present invention may come from any known sources and particular to known processes for the preparation of divinylarenes. For example, divinylarenes can be prepared with salt or metal wastes from arenes and ethylene.

The divinylarene reactant useful in the process of the present invention may be illustrated by general chemical Structures I-IV as follows:

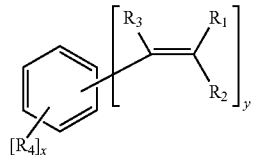

Structure I

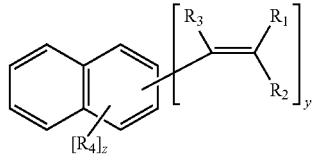

Structure II

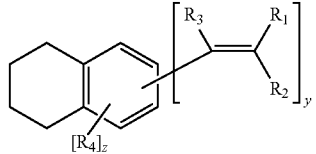

Structure III

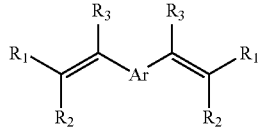

Structure IV

In the above Structures I, II, III and IV of the divinylarene reactant of the present invention, each $R_1$, $R_2$, $R_3$ and $R_4$ individually may be hydrogen, an alkyl, cycloalkyl, an aryl or an aralkyl group, wherein the alkyl, cycloalkyl, aryl, and aralkyl groups each individually may have from 1 to about 18 carbon atoms, and preferably from 1 to 4 carbon atoms; or a oxidant-resistant group including for example a halogen, a nitro, an isocyanate, or an R'O group, wherein R' may be an alkyl, aryl or aralkyl group each individually having from 1 to about 18 carbon atoms, and preferably from 1 to about 4 carbon atoms; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

In one embodiment of the present invention, the divinylarene useful in the present invention may comprise any substituted or unsubstituted arene nucleus bearing two vinyl (also referred to herein as "C═C bonds", "olefinic" or "ethylenic double bonds") groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example a saturated alkyl or an aryl, wherein the saturated alkyl may have from 1 to about 18 carbon atoms, and preferably from 1 to 4 carbon atoms, and the aryl may have from 1 to about 18 carbon atoms, and preferably from 6 to 10 carbon atoms; a halogen; a nitro; an isocyanate; or a R'O— group, wherein R' may be the same as defined above; or mixtures thereof. Ring-annulated benzenes may include for example naphthlalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by the dehydrogenation of diethylbenzene (DEB) may contain quantities of ethylvinylbenzene (EVB), naphthalene, polyethylbenzene (e.g. diethylbenzene, triethylbenzene, tetraethylbenzene, pentaethylbenzene, diphenylethane, other alkylated benzenes, and higher molecular weight oils), free radical inhibitors, or mixtures thereof.

In one embodiment of the present invention, DVB optionally containing EVB may be epoxidized. The DVB used can be a high purity DVB to make for example DVBDO, with a very low amount of ethylvinylbenzene oxide (EVBO). High purity with reference to DVB herein means, for example, a DVB which contains greater than about 80%, more preferably greater than about 90% and most preferably greater than about 95% DVB with the remainder being impurities or other compounds such as EVB.

The divinylarene used in the process of the present invention may include for example divinylbenzene, divinylnaphthalene, divinylbiphenyl, divinyldiphenylether, or mixtures thereof. In one preferred embodiment, the present invention uses divinylbenzene as the divinylarene reactant. In the embodiment using divinylbenzene as the divinylarene reactant, the divinylarene dioxide formed comprises divinylbenzene dioxide.

As aforementioned, the peroxycarboximidic acid reactant used in the present invention may be (i) pre-formed, (ii) formed in situ in the reaction mixture, or (iii) a combination of (i) and (ii). The peroxycarboximidic acid useful in the present invention may include for example a peroxycarboximidic acid reactant with the general chemical formula as follows:

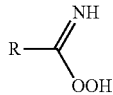

wherein R in the above structure may be a saturated hydrocarbon having from 1 to about 18 carbon atoms; preferably from 1 to about 6 carbon atoms, and more preferably from 1 to about 4 carbon atoms; or R may be an aromatic hydrocarbon having from 1 to about 18 carbon atoms; preferably from 1 to about 12 carbon atoms, and more preferably from 1 to about 6 carbon atoms; and wherein R is free of non-aromatic multiple bonds.

Examples of peroxycarboximidic acids useful in the present invention include, but are not limited to, peroxypropionimidic acid; peroxycapronimidic acid; peroxycaprinimidic acid; peroxytridecaneimidic acid; peroxy 1- and 4-methycyclohexanecarboximidic acid; peroxycyclohexaneacetimidic acid; or mixtures thereof.

In one embodiment of the process of the present invention, the epoxidation reaction can be represented by the following reaction Scheme I:

Scheme I

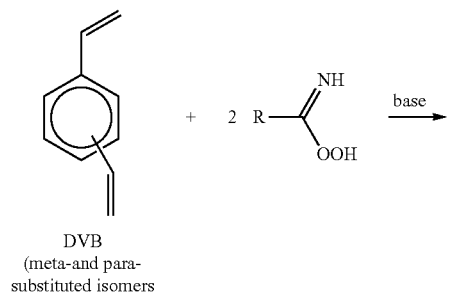

DVB
(meta- and para-substituted isomers

-continued

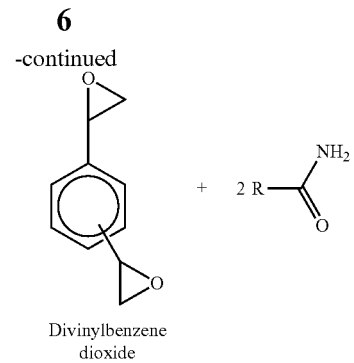

Divinylbenzene dioxide

The above example, Scheme I, shows the epoxidation process of the present invention wherein divinylbenzene (DVB) is epoxidized with a peroxycarboximidic acid having the following general formula:

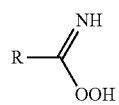

wherein R in the above structure may be the same as defined above.

As aforementioned, the peroxycarboximidic acid epoxidizing agents of the present invention can be obtained in various ways such as for example by pre-forming the peroxycarboximidic acid in a separate and independent reaction; or in situ in the reaction mixture. While separately pre-formed peroxycarboximidic acid can be successfully used in the reaction, the peroxycarboximidic acid epoxidizing agent is advantageously formed in situ in the reaction mixture. The peroxycarboximidic acid can be formed in situ in the reaction mixture for example by reacting a nitrile with hydrogen peroxide.

The present invention makes use of an in situ technique in carrying out the epoxidation by adding a nitrile and hydrogen peroxide ($H_2O_2$) to the divinylarene to be epoxidized, the peroxycarboximidic acid being formed from the nitrile and $H_2O_2$ under slightly basic conditions (e.g., a pH of at least greater than about 7 as measured by a pH meter) and simultaneously epoxidizing the divinylarene compound to form a divinylarene dioxide and an amide as products. In order to maintain the pH at greater than (>) about 7, a base may be added to the reaction mixture.

The nitrile compound employed in making the peroxycarboximidic acid in situ may be compounds in which the nitrile group is the only group capable of reacting with hydrogen peroxide. Especially useful nitriles may be those having the following formula:

wherein R in the above structure may be the same as defined above.

Nitriles in which the nitrile group is directly linked to an aromatic ring may be especially useful since these are known to form peroxycarboximidic acids which may be more active than the saturated nitriles and thus permit epoxidation in a shorter time, giving increased plant capacity.

Representative examples of nitriles used in the present invention, which on reaction with hydrogen peroxide advantageously make carboximidic acids for use as the epoxidizing agents of the present invention, include one or more of the following examples: aliphatic nitriles such as acetonitrile resulting in peroxyacetimidic acid with the following chemical structure:

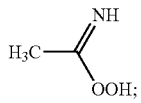

propionitrile resulting in peroxypropionimidic acid; capronitrile resulting in peroxycapronimidic acid; caprinitrile resulting in peroxycaprinimidic acid; tridecanenitrile resulting in peroxytridecaneimidic acid; cycloaliphatic nitriles such as 1- and 4-methylcyclohexanenitriles resulting in peroxy 1- and 4-methycyclohexanecarboximidic acids; cyclohexanenitrile resulting in peroxycyclohexaneacetimidic acid; aromatic nitriles such as ortho-, meta-, and para-tolunitriles, resulting in peroxyortho-, meta-, and para-toluimidic acids; and benzonitrile resulting in peroxybenzimidic acid with the following structure:

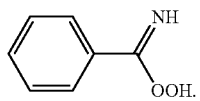

The above structure may be especially active as an epoxidizing agent.

Beta-hydroxynitriles readily obtained by reacting hydrogen cyanide with epoxy compounds may be another useful type of nitrile for use in the present invention. For example beta-hydroxypropionitrile which forms peroxybeta-hydroxypropionimidic acid by reaction with hydrogen peroxide can be used.

Polynitriles can also be used instead of mononitriles in making the peroxycarboximidic acids epoxidizing agents for use in the present invention. Polynitrile is defined as any molecule with two or more nitrile groups where in the nitrile groups are separated by 1 to 18 carbon atoms between the nitriles groups. For example dinitriles such as malononitrile, hexamethylene dicyanide, adiponitrile, and mixtures thereof can be used in the present invention. Soluble polyacrylonitriles may be another type of nitrile useful in the present invention.

In one preferred embodiment, the nitrile useful in the present invention may comprise acetonitrile, benzonitrile, propionitrile or mixtures thereof.

Especially useful peroxycarboximidic acids may be those having the following formula:

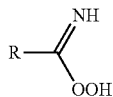

wherein R in the above structure may be the same as defined above.

In another embodiment, when the peroxycarboximidic acid is formed in situ in the reaction mixture for example by reacting a nitrile with hydrogen peroxide, the overall reaction of the process of the present invention taking place can be represented by the following reaction Scheme II:

Scheme II

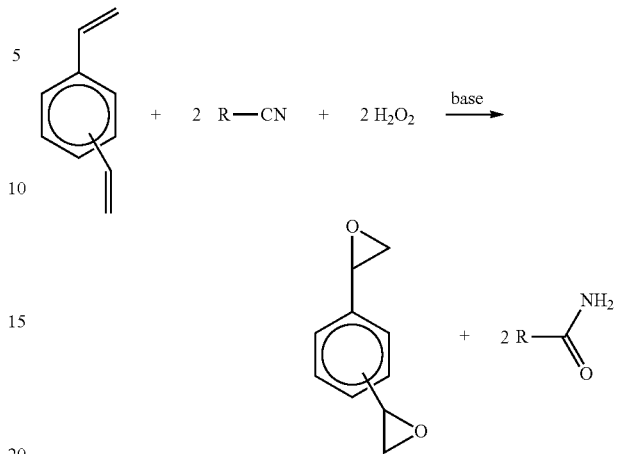

The above example, Scheme II shows an embodiment of the process of the present invention wherein divinylbenzene (DVB) is epoxidized and a peroxycarboximidic acid is formed in situ during the epoxidation. In Scheme II, R may be the same as defined above As aforementioned, the peroxycarboximidic acid can be prepared (pre-formed) prior to the use of such peroxycarboximidic acid in the reaction mixture by a separate reaction of a selected nitrile compound, such as for example any one or more of the nitriles described above, with hydrogen peroxide. Then the pre-formed peroxycarboximidic acid may be added to the divinylarene compound to be epoxidized with intimate mixing under reaction conditions. It may not be necessary in such a case to isolate the peroxycarboximidic acid in order to use it for the epoxidation in the presence of the required base.

An alternate method of making pre-formed peroxycarboximidic acid epoxidizing agent for use in the reaction of the present invention may be for example by reacting an imido acid chloride with a peroxide under basic conditions. For example, the imido acid chloride useful in the present invention may have the following general structure:

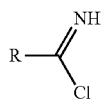

In one embodiment, hydrogen peroxide can be used alone or in combination with a base such as for instance, sodium hydroxide, sodium peroxide, sodium perborate, or the like, or mixtures thereof. R in the above structure may be the same as defined above.

Whether pre-formed or made in situ, at least one mole of the peroxycarboximidic acid per mole of epoxy group produced therewith may be generally used in the process of the present invention. However, different mole proportions of divinylarene compound to peroxycarboximidic acid epoxidizing agent can be employed. For example, it is often advantageous to employ a stoichiometric excess of one of the reactants in order to promote complete reaction of the other reactant at a faster rate. The divinylarene which is a component of the present invention contains two ethylenic double bonds. Generally, ratios of from about 0.25 mole to about 4 moles of peroxycarboximidic acid epoxidizing agent per mole of ethylenic double bond of the divinylarene may be used. In another embodiment of the process of the present invention, ratios of from about 0.75 mole to about 2 moles of peroxycarboximidic acid per mole of ethylenic double bond of the divinylarene may be used; and in yet another embodiment, ratios of from about 0.95 mole to about 1.30 mole of peroxycarboximidic acid per mole of ethylenic double bond of the divinylarene may be used.

In another embodiment, when the peroxycarboximidic acid is being formed in situ in the reaction mixture from a nitrile and hydrogen peroxide, generally ratios of about 0.25 mole to about 4 moles of hydrogen peroxide per mole of ethylenic double bond of the divinylarene may be used. In yet another embodiment, the mole ratio of hydrogen peroxide to ethylenic double bonds may comprise from about 0.5 mole to about 4.0 moles may be used. In still another embodiments of the process of the present invention, ratios of from about 0.75 mole to about 2 moles of hydrogen peroxide per mole of ethylenic double bond of the divinylarene may be used; ratios of from about 1.0 mole to about 2.0 moles of hydrogen peroxide per mole of ethylenic double bond of the divinylarene may be used in another embodiment; and ratios of from about 1.05 mole to about 1.30 mole of hydrogen peroxide per mole of ethylenic double bond of the divinylarene may be used in still another embodiment.

In order to illustrate one advantage of using the above stated ratios of hydrogen peroxide per mole of ethylenic double bond, the sequential epoxidation of both ethylenic double bonds of, for example, DVB with a peroxycarboximidic acid can be shown as Schemes III and IV which follow; said sequential epoxidation representing one embodiment of the process of the present invention:

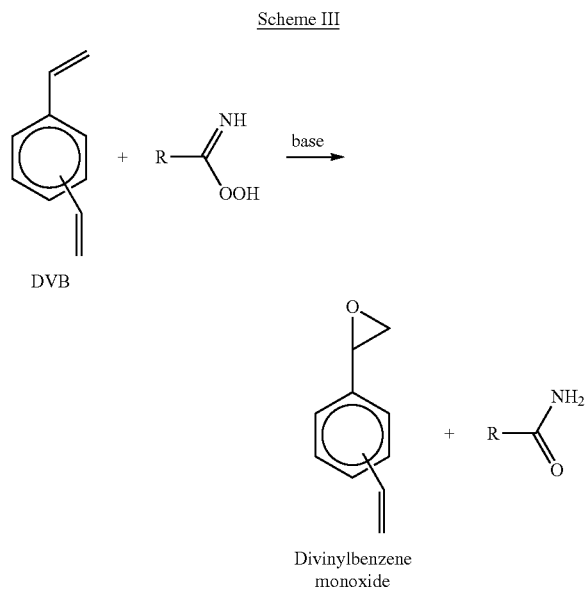

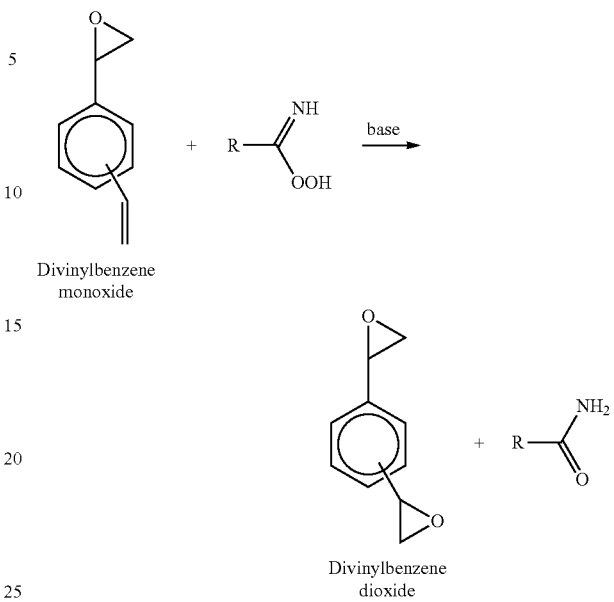

In the above example of the sequential epoxidation, illustrated by Schemes III and IV, divinylbenzene (DVB) is reacted with a peroxycarboximidic acid forming a divinylbenzene monoxide and an amide (Scheme III) followed by further reaction of the monoxide with a peroxycarboximidic acid forming a divinylbenzene dioxide and an amide (Scheme IV). In the above chemical structures of equations, Scheme III and IV, R may be the same as defined above.

It has been found that if a high degree of reaction of ethylenic double bonds to epoxide groups is not obtained, then a substantial amount of divinylarene and/or divinylarene monoxide may remain in the reaction product. The above stated ratios of hydrogen peroxide to ethylenic double bond advantageously may give a high degree of reaction to the desired divinylarene dioxide.

Regardless of whether the peroxycarboximidic acid is (1) made in situ or (2) preformed, if a mole excess of ethylenic double bonds to hydrogen peroxide is used, then a large amount of divinylarene starting material and divinylarene monoxide may remain at the end of the epoxidation reaction; and separation of a significant amount of divinylarene and divinylarene monoxide from the divinylarene dioxide to obtain a purified product of divinylarene dioxide may be required. Therefore, it may be advantageous to use a slight mole excess of hydrogen peroxide relative to ethylenic double bonds in the process of the present invention, in order to obtain high conversion of ethylenic double bonds to epoxide groups while not using an undue excess of hydrogen peroxide, so that both desired embodiments, high conversion of ethylenic double bonds to epoxide groups and minimal use of hydrogen peroxide can be achieved.

An embodiment of the present invention includes for example a process for epoxidation of divinylarenes with a peroxycarboximidic acid, pre-formed or formed in situ, which uses a ratio of about 1.0 mole to about 2.0 moles of hydrogen peroxide per mole of ethylenic double bond, and more preferably a ratio of about 1.05 mole to about 1.30 moles of hydrogen peroxide per mole of ethylenic double bond, with the reaction conducted at the conditions described herein for the process of the present invention.

The process of the present invention advantageously provides one or more, and preferably all, of the following results:

(1) The conversion of charged divinylarene may comprise greater than about 80% conversion of in one embodiment; greater than about 90% conversion in another embodiment; greater than about 98% conversion in yet another embodiment; and, greater than about 99% conversion of charged divinylarene in still another embodiment. An objective of the present process is to obtain a 100% conversion of charged divinylarene, and generally the conversion of charged divinylarene may be from about 80% to about 100% conversion in one embodiment; from about 90% to about 100% conversion in another embodiment; from about 98% to about 100% conversion in yet another embodiment; and from about 99% to about 100% in still another embodiment.

(2) The percent yield of an intermediate divinylarene monoxide based on charged divinylarene may comprise less than about 50% in one embodiment; less than about 20% in another embodiment; less than about 10% in yet another embodiment; and less than about 5% in still another embodiment. In another embodiment, the percent yield of divinylarene monoxide based on divinylarene may comprise from about 0.1% to about 50%; from about 0.1% to about 20% in another embodiment; from about 0.1% to about 10% in yet another embodiment; from about 0.1% to about 5% in still another embodiment; and from about 0.1% to about 2% in still another embodiment.

(3) The percent yield of divinylarene dioxide product based on divinylarene may comprise greater than about 50% yield in one embodiment; greater than about 60% yield in another embodiment; greater than about 70% yield in yet another embodiment; and greater than 80% yield of divinylarene dioxide in still another embodiment. An objective of the present process is to obtain a 100% yield of divinylarene dioxide product, and generally the percent yield of divinylarene dioxide product based on divinylarene may comprise from about 50% to about 100% yield of divinylarene dioxide; from about 60% to about 100% yield in another embodiment; from about 70% to about 100% yield in another embodiment; and from about 80% to about 100% yield in yet another embodiment.

(4) The percent yield of epoxide groups based on charged hydrogen peroxide; may comprise greater than about 50% yield of epoxide groups in one embodiment, greater than about 60% yield in another embodiment; greater than about 70% yield of epoxide groups in yet another embodiment; and greater than about 90% in still another embodiment. An objective of the present process is to obtain a 100% yield of epoxide groups based on charged hydrogen peroxide, and generally the percent yield of epoxide groups may comprise from about 50% to about 100% yield; from about 60% to about 100% yield in another embodiment; from about 70% to about 100% yield in yet another embodiment; and from about 90% to about 100% yield in still another embodiment.

In an embodiment wherein the peroxycarboximidic acid is being formed in situ in the reaction mixture from a nitrile, in general, mole ratios of nitrile to hydrogen peroxide of from about 0.5:1 to about 4:1 can be used; preferably ratios of nitrile to hydrogen peroxide of from about 1:1 to about 3:1 can be used; and more preferably ratios of nitrile to hydrogen peroxide of from about 1.2:1 to about 2.5:1 can be used. In such cases the ranges of hydrogen peroxide to ethylenic double bonds of the divinylarene may be in the range described above for the process of the present invention. When employing a polynitrile for in situ formation of the epoxidizing agent by reaction with hydrogen peroxide, mole proportions which take into account the number of nitrile groups per mole of the starting nitrile should be used.

The nitrile compounds employed in making the peroxycarboximidic acid may be nitrile compounds in which the nitrile group in such compound is the only group capable of reacting with hydrogen peroxide.

The reaction may be preferably carried out in the liquid phase using a solvent wherein the solvent may include water and/or one or more organic solvents suitable for the reactants. For example, aqueous solutions of hydrogen peroxide and/or basic compounds may be used in the present invention. When epoxidizing divinylarene compounds of low solubility in water and/or using peroxycarboximidic acids which are substantially water insoluble, an organic solvent for the reaction may be useful instead of, or together with, water. Alcohols, particularly water soluble alcohols, may be useful solvents, including methanol, ethanol, isopropanol, 1-methoxy-2-propanol, isobutyl alcohol, tert-butyl alcohol, or mixtures thereof. Polyhydric alcohols, for instance, ethylene glycol, 2-methyl-2,4-pentanediol, or mixtures thereof can be used. Hydrocarbon solvents, such as for example aromatic hydrocarbon solvents including toluene, benzene, xylenes, and the like; or aliphatic hydrocarbon solvents including pentane, hexane, cyclohexane, and the like; or mixtures thereof, can be used in the present invention. Other non acidic solvents can be used such as ketones; ethers; chlorinated solvents; esters or mixtures thereof. For example, the solvents useful in the present invention may include acetone, methyl ethyl ketone, 4-methyl-2-pentanone, cyclohexanone, diacetone alcohol, dimethyl ether, ethylene glycol monomethyl ether, ethylene glycol monoacetate, ethyl acetate, dioxane, methylene chloride, chloroform, or mixtures thereof. Solvents which are free from polymerizable ethylenic linkages may also be used in the present invention process.

In one preferred embodiment, the reaction solvent may comprise for example, methanol, isopropanol, diethyl ether, benzene, toluene, ethyl acetate, 4-methyl-2-pentanone, 1-methoxy-2-propanol, or mixtures thereof.

Generally, when the reaction is carried out with amounts of liquid organic solvents, the weight ratio of the organic solvent to divinylarene may be less than about 20, preferably less than about 10, and more preferably less than about 5. In other embodiments of the present invention, the weight ratio of the organic solvent to divinylarene may be from about 0.1 to about 20, preferably from about 0.5 to about 10, and more preferably from about 1 to about 5.

Another embodiment of the present invention includes for example the use of the above described nitriles both as a reactant and as a reaction solvent for the composition of the present invention. In this instance, an excess of nitrile can be used in order to provide both the needed reaction and the functionality of the nitrile to function as a solvent, wherein the excess of nitrile falls within the above discussed ranges of weight ratios.

The reaction phase can be single phase or multiphase, that is, the reaction mixture can be a single homogeneous phase or the reaction mixture may comprise more than one liquid and/or solid phases.

For maintaining the pH of the reaction mixture at a pH of greater than about 7, an organic or inorganic basic compound can be added to the reaction mixture. Both substantially soluble and substantially insoluble basic compounds may be effective, provided the basic compound maintains the required pH of the reaction mixture. Because basic inorganic compounds may be readily availability at low cost, basic inorganic compounds may be generally advantageous.

Suitable basic compounds include for example, inorganic hydroxides, examples of which may be alkali and alkaline earth hydroxides such as sodium hydroxide, potassium hydroxide, ammonium hydroxide, magnesium hydroxide, calcium hydroxide, and the like, or mixtures thereof; the corresponding oxides of alkali and alkaline earth metals, for example, sodium oxide, calcium oxide, magnesium oxide, and the like, or mixtures thereof; and basic salts such as water-soluble carbonates, bicarbonates, phosphates and the like, examples of which may be sodium carbonate, sodium bicarbonate, potassium bicarbonate, tripotassium phosphate, and the like; or mixtures thereof.

In one preferred embodiment, the basic compound may comprise a hydroxide, a bicarbonate, or mixtures thereof; more specifically, the basic compound may comprise an alkali metal hydroxide, an alkali metal bicarbonate, or mixtures thereof in another embodiment; and even more specifically, the basic compound may comprise sodium hydroxide, potassium hydroxide, sodium bicarbonate, potassium bicarbonate, and mixtures thereof in yet another embodiment.

Organic basic compounds used in the present invention, in general, may be less preferred because of their higher cost than inorganic bases. However, organic bases may still be useful in the present invention. Among the organic basic compounds which may be used in the present invention, include, for instance, salts of phenols such as potassium phenates, calcium phenates, sodium meta-methyl phenoxide, sodium naphthoxide, amines such as methylamine, dimethylamine, trimethylamine, and higher analogues such as triethylamine, tri-n-propylamine, tri-n-butylamine and the like; or mixtures thereof.

Aqueous solutions of any water-soluble basic compounds may be used in the present invention composition; and can range generally from about 0.1 wt % to about 50 wt %; preferably from about 1 wt % to about 40 wt %, and more preferably from about 4 wt % to about 10 wt % in the composition.

In some embodiments, there may be operating advantages in using an insoluble form of the basic compound. For example, anion exchange resins, especially amine or quaternary ammonium base resins may be a particularly convenient form of insoluble base for use in the process of the present invention. Examples of these suitable base resins may include, for instance, the amination products of chloromethylated styrene-divinylbenzene copolymers described in U.S. Pat. No. 2,591,573, incorporated herein by reference; resins made by the process of U.S. Pat. No. 2,388,235, incorporated herein by reference; anion resins; and weak base ion exchange resins; and the like, or mixtures thereof. The base resins may be used in the free base form or in the form of the salts, for instance, the carbonate salts of the strong base resins. Another class of insoluble basic compounds useful in the present invention may include for example hydrotalcites, which are synthetic anionic clays with Brucite-like layers having positive charge with anionic species in the interlayer, for example the hydrotalcite $Mg_{10}Al_2(OH)_{24}CO_3$ described in K. Kaneda et al., Chem. Commun., 1998, pp. 295-296 and prepared by the references cited therein; incorporated herein by reference.

The rate of the present invention reaction is pH dependent, and a pH of at least greater than about 7 and preferably greater than about 9 may be desired in order to promote rapid reaction. Generally, the pH of the reaction mixture may comprise a pH of between greater than about 7 up to about 12. In one embodiment, the basic compound is used to maintain the pH of the reaction mixture at from about 9 to about 11.5. In another embodiment, beneficial results may be obtained when the addition of the basic compound is controlled so as to maintain the pH of the reaction mixture in the range of from about 9 to about 10.5. In another embodiment, the pH of the reaction may be maintained in the range of about 9.5 to about 10.5. In a preferred embodiment, the pH of the reaction is maintained in the range of about 9.5 to about 10.1. The term "pH" herein means the pH as measured in the reaction solution at the reaction temperature by a pH meter equipped with a Thermoscientific #8272BN pH probe, which may be calibrated using standard pH 7 and pH 10 buffers obtained from Fisher Scientific. A basic compound addition profile with one or more constant addition rates, or intermittent additions, may be used as an alternative system to pH control. In one embodiment, the at least one basic compound may be rate added or added all at once to the initial reaction sufficient to maintain the pH of the reaction mixture in the range of for example from about 7 to about 12. The basic compound may be for example sodium hydroxide (NaOH).

Whether pH control or a NaOH addition profile is used, the total NaOH added is generally in the range of from about 0.01 mole to about 0.15 mole of NaOH per mole of total hydrogen peroxide added; preferably from about 0.02 mole to about 0.10 mole of NaOH per mole of total hydrogen peroxide added; and more preferably in the range of from about 0.04 mole to about 0.08 mole of NaOH per mole of total hydrogen peroxide added.

The reaction temperature of the reaction process of the present invention may vary depending on factors such as the particular nitrile and basic compound being used. Generally, the temperature of the reaction may be maintained between about 20° C. and about 100° C. Temperatures in the range of from about 0° C. to about the boiling temperature of the mixture at the operating pressure can be employed, although temperatures of the order of about 20° C. to about 100° C. may usually be used, preferably in a temperature range of from about 20° C. to about 60° C.; and more preferably in a temperature range of from about 40° C. to 50° C. In general, the higher the reaction temperature of the present invention process, the shorter will be the reaction time necessary to obtain higher conversion of olefins. For example, reaction times as long as about 24 hours may be used at about 20° C., whereas when less than about 6 hours reaction time is desirable, the reaction temperature may be increased to about 50° C. In another embodiment, when operating above the boiling point of one or more reactants or solvents, it may be preferred to operate under sufficient pressure to maintain the reactants at least partially in the liquid phase.

In a different embodiment, the temperature of the process of the present invention may be controlled by carrying out the process at less than atmospheric pressure by applying vacuum in order to induce boiling of a low boiling component of the reaction mixture, wherein at least a portion of vapors formed by boiling of the low boiling component are condensed; and then optionally, the condensed vapors are recycled to the reaction mixture.

In the case of the epoxidation of divinylarenes which may be prone to free radical polymerization, temperatures of less than about 70° C. may be generally used to avoid undesired polymerization of the ethylenic double bonds, although temperatures of less than about 60° C. may be more preferred in another embodiment.

Numerous additives can optionally be employed as part of the present invention including for example a free radical polymerization inhibitor. For example, one or more free radical polymerization inhibitors may be added to any of the steps of the process of the present invention including for instance the reaction step, the recovery step and/or the purification step. The inhibitor may comprise a phenol; a hydroquinone; a quinone; an aromatic nitro compound, a nitrophenol, an amine; a nitroso compound; a nitroxide; or mixtures thereof.

Free radical polymerization inhibitors which may be employed in the present invention, include for example phenols such as 4-methoxy phenol, 4-tert-butylcatechol, or 2,6-di-tert-butyl-4-methylphenol; hydroquinones such as 1,4-dihyrdroxybenzene or 3,5-di-tert-butylbenzene-1,2-diol; quinones such as 1,4-benzoquinone or naphthalene-1,2-dione; aromatic nitro compounds such as 1,3-dinitrobenzene or 1,4-dinitrobenzene; nitrophenols such as 2-(sec-butyl)-4,6-dinitrophenol, 4-methyl-2-nitrophenol, or 4-methyl-2,6-dinitrophenol; amines such as phenothiazine, $N^1$-phenyl-$N^4$-propylbenzene-1,4-diamine, N-(1,4-dimethylpentyl)-N' phenyl-p-phenylenediamine, N,N-diethylhydroxylamine, or 2,2,6,6-tetramethylpiperidine; nitroso compounds such as N-nitrosophenylhydroxylamine ammonium salt; nitroxide compounds (described in detail herein below); or mixtures thereof.

Nitroxide compounds are a class of free radical polymerization inhibitors which are especially useful in the present invention. The term "nitroxides" as used here is synonymous with the terms "aminoxyl", "nitroxyl", or "hindered amine nitroxyl radicals" which are often used in the art. The nitroxides in general are compounds having at least one NO* group, where the * asterisk denotes an unpaired electron, and the nitrogen atom is bonded to two carbon atoms, to neither of which hydrogen atoms are attached. The nitroxide compounds useful in this invention have the generic structure:

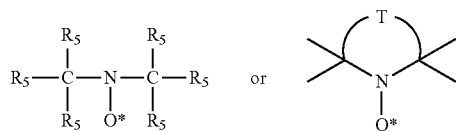

where each $R_5$ individually is an alkyl group of 1 to 18 carbon atoms and T is a group required to form a 5 or 6 member ring. Two or more nitroxyl groups may be present in the same molecule by linking two of the ring structures above through the T moiety by a linking group. Preferably, the nitroxides are selected from the group consisting of:

1-oxyl-2,2,6,6-tetramethylpiperidine (also referred to in the art as TEMPO),
1-oxyl-2,2,6,6-tetramethylpiperidin-4-ol (also referred to in the art as 4-hydroxy TEMPO),
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-n-butoxypiperidine,
1-oxyl-2,2,6,6-tetramethyl-4-allyloxy-piperidine,
1-oxyl-2,2,6,6-tetramethyl-4-acetamidopiperidine,
1-oxyl-2,2,6,6-tetramethylpiperidin-4-(N-butylformamido) piperidine,
1-oxyl-2,2,6,6-tetramethyl-4-(2-methoxyethoxyacetoxy)piperidine,
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-(1-oxyl-2,2,6,6-tetramethylpiperidin-4-yl) adipamide,
N-(1-oxyl-2,2,6,6-tetramethylpiperidin-4-yl) caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl)]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy)piperidine,
1-oxyl-2,2,6,6-tetramethyl-4-(2-hydroxy-4-oxapentoxy)piperidine, and di-tert-butyl nitroxyl.

In one preferred embodiment, the nitroxide useful in the present invention may be selected from the group consisting of bis(1-oxyl-2,2,6,6-tetramethylpiperidin-4-yl) sebacate; 1-oxyl-2,2,6,6-tetramethylpiperidine; 1-oxyl-2,2,6,6-tetramethylpiperidin-4-ol; 1-oxyl-2,2,6,6-tetramethyl-4-n-butoxypiperidine; and mixtures thereof.

A combination of inhibitors from within the same class (e.g. nitroxides), as described above, may be used; or a combination of inhibitors from above different classes may be used, for instance a phenolic inhibitor may be used in combination with a nitroxide. In one embodiment, a combination of 4-tert-butylcatechol with either bis(1-oxyl-2,2,6,6-tetramethylpiperidin-4-yl) sebacate or 1-oxyl-2,2,6,6-tetramethylpiperidin-4-ol is used to inhibit free radical polymerization in the reaction to make a divinylarene oxide such as DVBDO.

The free radical polymerization inhibitors introduced in the reaction step can be added in various forms (e.g., the inhibitor in its pure form or as a solution dissolved in a solvent) and with various methods of addition (such as for example: all at once, continuous, or intermittent). The concentration of the inhibitors useful in the present invention can be for example from about 0.01 wt % up to about 5 wt % based on total divinylarene added in the reaction. Preferably in another embodiment, the concentration of the inhibitors may be in the range of from about 0.1 wt % to about 2.0 wt % based on total divinylarene added in the reaction.

The inhibitors may be added all at the beginning of the reaction (prior to heating), intermittently (e.g. every 30 minutes), or continuously. A combination of addition methods can be used, for instance a portion of the total inhibitor may be added at the beginning of the reaction and the remaining portion of inhibitor can be added continuously during the reaction. When adding the inhibitor intermittently or continuously, the proportion of the total inhibitor added per time can be linear or non-linear. If using continuous inhibitor addition, the addition may be stopped for periods of time, especially toward the end of the reaction, which may give a higher efficiency of the inhibitor usage without sacrificing yield of the desired product.

The free radical polymerization inhibitor can be introduced either in its pure form or as a solution in a suitable solvent. The solvent used with the inhibitor can be for example any one or more of the same reaction solvents described above. For example, inhibitors can be introduced as solutions in any suitable solvent, including for instance water, methanol, acetonitrile, alkyl vinylarene monoxide (e.g. ethyl vinyl benzene monoxide), divinylarene (e.g. divinylbenzene), divinylarene monoxide (e.g. divinylbenzene monoxide), divinylarene dioxide (e.g. divinylbenzene dioxide), or mixtures thereof. In one embodiment, the inhibitor can be for example 1-oxyl-2,2,6,6-tetramethylpiperidin-4-ol, and can be introduced as a 20% solution in water during the reaction step.

In one preferred embodiment, the total amount of the free radical polymerization inhibitor added to the reaction mixture may comprise from about 0.01 wt % to about 5.0 wt % based on the total divinylarene added in the reaction. In another embodiment, the total amount of the free radical polymerization inhibitor added to the reaction mixture may be from about 0.1 wt % to about 2.0 wt % based on the total divinylarene added in the reaction. The free radical polymerization inhibitor may be added to the reaction mixture all at once, intermittently, continuously, or using a combination of addition methods, wherein the inhibitor may be added either in its pure form or in a suitable solvent.

In one preferred embodiment, the free radical polymerization inhibitor may comprise 1-oxyl-2,2,6,6-tetramethylpiperidine, or a substituted form of 1-oxyl-2,2,6,6-tetramethylpiperidine. In another embodiment, the free radical polymerization inhibitor may comprise 1-oxyl-2,2,6,6-tetramethylpiperidin-4-ol; 1-oxyl-2,2,6,6-tetramethyl-4-n-butoxypiperidine; bis(1-oxyl-2,2,6,6-tetramethylpiperidine-4-yl) sebacate; 4-tert-butylcatechol; or mixtures thereof. In yet another embodiment, the free radical polymerization inhibitor may comprise bis(1-oxyl-2,2,6,6-tetramethylpiperidine-4-yl) sebacate which can be added intermittently or continuously over the course of the reaction at a total amount added to the reaction mixture of for example from about 0.1 wt % to about 2.0 wt % based on the total divinylarene added in the reaction. In still another embodiment, the free radical polymerization inhibitor may comprise 1-oxyl-2,2,6,6-tetramethylpiperidin-4-ol which can be added intermittently or continuously over the course of the reaction at a total amount added to the reaction mixture of for example from about 0.1 wt % to about 2.0 wt % based on the total divinylarene added in the reaction.

In another embodiment, the process of the present invention can employ a free radical inhibitor alone or in combination with an oxygen-containing gas; or the process can employ an oxygen-containing gas alone. In general, the oxygen-containing gas may be an oxygen-nitrogen gas mixture. In one embodiment, the oxygen-nitrogen gas mixture may comprise up to about 21% oxygen with the balance being nitrogen. In another embodiment, the oxygen-containing gas may be an oxygen-nitrogen gas mixture comprising up to about 10% oxygen with the balance being nitrogen. Generally, the flow rate of the gas mixture may comprise from about 0.01 to about 1.0 times the total reactor volume per minute.

In one embodiment, in conjunction with using free radical inhibitors that may require oxygen for activity, a vapor phase of the process can also include up to about 21% oxygen, with the balance comprising nitrogen. In other embodiments, the oxygen content of the gas may be generally up to about 21%, preferably up to about 10%, and more preferably up to about 5% with the balance being nitrogen or optionally another inert gas or mixtures of inert gases.

In another embodiment, the oxygen-containing gas may be introduced directly into a liquid phase of the process, optionally with stirring to help disperse the gas throughout the liquid phase in order to enhance the oxygen absorption into the liquid phase. In one preferred embodiment, a gas composition with about 5% oxygen, with the balance nitrogen, is introduced continuously into the reaction directly into the liquid phase. The flow rate of the gas can be from about (0.01×the total reactor volume) per minute up to about (1.0×the total reactor volume) per minute. In another more preferred embodiment, the flow rate can be from about (0.05×the total reactor volume) per minute up to about (0.5×the total reactor volume) per minute.

Water may optionally be added to the initial reaction mixture (prior to addition of hydrogen peroxide or pre-formed peroxycarboximidic acid), generally, in an amount of from about 1 wt % to about 8 wt % with respect to the weight of initial reaction mixture.

Buffering agents such as alkali phosphates may also be optionally added to the reaction mixture in combination with the basic compounds. Alkali phosphates which can be used in the present invention include for example sodium dihydrogen phosphate ($NaH_2PO_4$); potassium dihydrogen phosphate ($KH_2PO_4$); disodium hydrogen phosphate ($Na_2HPO_4$) either as its anhydrous or hydrated forms, for instance the dodecahydrate $Na_2HPO_4 12H_2O$; dipotassium hydrogen phosphate ($K_2HPO_4$); or mixtures thereof.

Chelating agents such as ethylenediaminetetraacetic acid or its dialkaline salt (e.g. disodium) may optionally be added to the initial reaction mixture in an amount from about 0.01 wt % to about 1 wt % with respect to the weight of hydrogen peroxide.

The reaction of the present invention may be carried in various ways including for example, as a batch process, as a semi-batch process, as a continuous process, or a combination thereof. Batch, intermittent, or continuous methods of reaction can be employed in the present invention; and the reactants can be introduced into the reaction mixture in any convenient order. In one preferred embodiment, the reaction may be carried out in (i) a batch fashion; or (ii) a continuous fashion. One advantageous method of batchwise reaction, when employing the procedure of in situ formation of the peroxycarboximidic acid epoxidizing agent, comprises adding hydrogen peroxide to the reaction mixture, for example, advantageously commercial aqueous hydrogen peroxide solution of about 30% to about 75% concentration, to a stirred mixture of the divinylarene compound being epoxidized, and an organic nitrile in a solvent containing sufficient base to bring the initial pH within the range in accordance with the present invention. Preferably the reaction mixture may be cooled while the hydrogen peroxide feed rate may be controlled so as to maintain the desired reaction temperature. Additional base can also be fed to the reaction mixture as needed to maintain the pH of the mixture within the range in accordance with the present invention. In an alternate embodiment, the total amount of the basic compound may be added to the reaction mixture at the start of the reaction in this method of operation. For example, basic acting salts, such as sodium bicarbonate, potassium phenoxide, sodium acetate, and the like; or mixtures thereof, may be used for maintaining the desired pH of the reaction in this way.

Alternatively, the reaction can be carried out by charging pre-formed peroxycarboximidic acid and a suitable solvent of the previously indicated type to a stirred reactor provided with temperature control means, suitably an autoclave, preferably with the desired base. Then, the divinylarene compound to be epoxidized may be fed into the reactor with or without additional basic compound as needed to maintain the pH of the reaction mixture within the preferred range until a reactor charge has been completed. For either order of addition above, it may be usually desirable to continue stirring the reaction mixture at the reaction temperature for a period of time after all of the reactants have been added in order to promote the desired degree of reaction, optionally with additional basic compound added to maintain the pH within the preferred range.

The process of the present invention can be carried out continuously in a stirred reactor, for example, by partially reacting an initial charge as described above, then continuously adding divinylarene compound, hydrogen peroxide, and organic nitrile separately to the reactor with continuous or intermittent addition of base in the preferred amount while continuously or intermittently withdrawing divinylarene oxide containing reacted mixture from the reactor. The same beneficial result can be obtained, by using at least one continuous stirred tank reactor (CSTR), or at least one plug flow reactor (PFR), or at least one loop reactor or a combination thereof, with or without external exchangers either in series or in parallel. At least one pump can be used to circulate the reaction mixture through the reactor as a continuous stream into which the divinylarene compound being epoxidized, hydrogen peroxide, nitrile and basic compound may be continuously fed at separate points sufficiently separated from the point of withdrawal of reaction mixture such that substantial reaction may be achieved before removal of the product-containing mixture from the reactor.

Alternatively, the divinylarene compound can be fed at spaced points along the path of flow of the reaction mixture through a tubular or other suitable form of reactor in which the proper temperature may be maintained. Temperature control can be achieved by external cooling or evaporation of a volatile component of the mixture, for instance, a liquefied gaseous hydrocarbon such as butane or isopentane, which can also serve at least in part as the solvent and/or diluent for the reactants, the pressure of the system being regulated so that this volatile component will evaporate at the desired reaction temperature. As in the previously described modification of the process, hydrogen peroxide solution and/or a solution of the base being used can be fed, preferably separately, into the stream of reaction mixture at intermediate points between the points at which the divinylarene compound being epoxidized is fed. In any of these methods of operation a feed stream of pre-formed peroxycarboximidic acid can be substituted for the hydrogen peroxide and nitrile feeds. Advantageously, the peroxycarboximidic acid epoxidation agent may be fed as the crude reaction mixture in which it is produced, preferably at the alkaline pH at which the epoxidation is preferably conducted as previously described above.

The removing step (b) of the present invention process may be carried out, for example, by evaporation. In one embodiment, the evaporation process may be carried out under vacuum. In another embodiment, the vacuum evaporation of step (b) may comprise a distillation process. For example, in one preferred embodiment, step (b) may be carried out at a temperature of from about 5° C. to about 100° C.; and at a pressure of from about 0.1 mmHg (13 Pa) to about 200 mmHg (26600 Pa); or at a temperature of from about 30° C. to about 60° C.; and at a pressure of from about 0.1 mmHg (130 Pa) to about 50 mmHg (6700 Pa) in another embodiment.

In another embodiment, the process of the present invention includes a vacuum separation step (b) comprising for example vacuum stripping the reaction effluent of step (a) to remove "lights" from the divinylarene oxide; wherein a biphasic concentrate is formed; and wherein the concentrate separates into (b1) an organic phase and (b2) an aqueous phase; said organic phase being rich in divinylarene oxide product.

For example, in one embodiment, the epoxidation reaction effluent from step (a) can be for example a crude divinylarene oxide product. In the present invention, the reaction effluent of the above divinylarene oxide synthesis process may be a reaction product mixture, i.e., wherein in one embodiment the major components of the effluent can be for example DVBDO/divinyl benzene monoxide (DVBMO)/EVBMO (products), methanol, water, acetonitrile and acetamide (by-product) in one liquid phase.

In one embodiment, the process of the present invention may be carried out such that greater than about 50 percent of the mass of the at least one divinylarene oxide in the reaction effluent of step (a) is present in the organic phase after step (b). In another embodiment, the mass of the at least one divinylarene oxide in the reaction effluent of step (a) is present in the organic phase after step (b) may be greater than about 70 percent; greater than about 80 percent in yet another embodiment; and greater than about 90 percent in still another embodiment.

In addition, the process of the present invention may be carried out such that greater than about 50 percent of the mass of the at least one amide in the reaction effluent of step (a) is present in the aqueous phase after step (b). In another embodiment, the mass of the at least one amide in the reaction effluent of step (a) is present in the aqueous phase after step (b) may be greater than about 70 percent; greater than about 80 percent in yet another embodiment; and greater than about 90 percent in still another embodiment.

Another embodiment of the present invention process includes removing at least a portion of one or more of methanol, water and acetonitrile in step (b).

The process of the present invention comprises vacuum separating the epoxidation reaction effluent from step (a) to remove for example at least a portion of and preferably most of the solvent(s) such as methanol and the nitrile compound(s) such as acetonitrile present in the reaction mixture. The remaining reaction product after vacuum stripping separates into an oxide-rich organic phase such as a DVBDO-rich organic phase and an amide-rich aqueous phase such as an acetamide-rich aqueous phase. As described herein below, the organic phase and the aqueous phase formed after vacuum stripping can be separated from each other by any well known suitable means such as for example by gravity (decanting, coalescing) or by centrifugation. Generally, the vacuum stripping step may be carried out at a temperature of from about 0° C. to about 195° C. in one embodiment; from about 5° C. to 100° C. in another embodiment; and from about 30° C. to about 60° C. in yet another embodiment. The vacuum stripping step may be generally carried out at a pressure from about 0.1 mmHg (13 Pa) to about 700 mmHg (93300 Pa) in one embodiment; from about 0.1 mmHg (13 Pa) to about 200 mmHg (26700 Pa) in another embodiment; and from about 0.1 mmHg (13 Pa) to about 50 mmHg (6700 Pa) in yet another embodiment.

The vacuum separation can be carried out in suitable equipment known to those skilled in the art such as for example a vessel (e.g. an agitated tank, a reactor), a distillation column, a wipe film evaporator, a flash evaporator, or a combination thereof.

Thermal treatment of the reactor effluent prior to or during the evaporation of the "lights" for extended time can result in alcoholysis or hydrolysis of the epoxide groups produced in the reaction step (a). As a result, the evaporation may be done under high vacuum conditions for longer residence times at lower temperatures or under flash conditions for shorter residence times at higher temperatures.

In one embodiment of the present invention, the evaporation occurs at absolute pressures of between about 50 mmHg (6700 Pa) and about 500 mmHg (67000 Pa) and at temperatures of between about 0° C. and about 60° C. for a time of from about 1 second to about 12 hours. In a preferred embodiment, the evaporation occurs at pressures of between about 100 mmHg (13300 Pa) and about 200 mmHg (26700 Pa) and at temperatures of between about 30° C. and about 60° C. at a time of from about 1 second to about 4 hours. The equipment that may be used for such an embodiment may be a vessel with associated heat exchangers or a heated jacket on the vessel. Preferably, the fluid in the vessel is circulated inside the vessel and past the heat exchange surfaces by an agitator, a pump or a thermosyphon, or a combination thereof. The evaporation is considered complete when, for example, the residual acetonitrile content is below about 5 wt %.

In another embodiment of the invention, the evaporation occurs at absolute pressures of less than about 40 mmHg (5300 Pa); at temperatures of between about 60° C. and about 200° C.; and at residence times of from about 1 second to less than about 10 minutes. Preferably in this embodiment, the evaporation occurs at temperatures of between about 60° C. and about 80° C.; at pressures of less than about 40 mmHg (5300 Pa); and at residence times of from about 1 second to less than about 10 minutes. The evaporation is considered complete when, for example, the residual acetonitrile content is below about 5 wt %. The equipment that may be used for such an embodiment may be a falling film evaporator, a distillation column, a wiped film evaporator, a flash evaporator or a combination thereof.

Optionally, a stripping agent may be added to the reactor effluent to facilitate the vacuum stripping. An inert gas, such as nitrogen, argon or $CO_2$, may be used as stripping agents. Liquid stripping agents useful in the present invention may include for example lower alkanes having from 1 to about 6 carbon atoms; ethers such as dimethylether, diethylether, and methyl tert-butylether; ketones such as acetone, methylethyl ketone, and methylisobutyl ketone (MIBK); or mixtures thereof.

Optionally, the reactor effluent may be neutralized to a pH of between about 6.5 and about 8 prior to the evaporization step to reduce the rate of hydrolysis or alcoholysis.

In carrying out the process of the present invention, the organic phase and the aqueous phase formed after the vacuum evaporation may be separated in a separation step. Generally, the phase separation step of the process of the present invention may be carried out at a temperature of from about 0° C. to about 60° C. in one embodiment; from about 25° C. to about 50° C. in another embodiment; and from about 35° C. to about 45° C. in yet another embodiment. The pressure of the separation step may be generally from about 0.5 atmospheres (atm) (50.7 kPa) to about 10 atm (1013.3 kPa) in one embodiment; from about 1 atm (101.3 kPa) to about 5 atm (506.6 kPa) in another embodiment; and from about 0.5 atm (50.7 kPa) to about 1.5 atm (152.0 kPa) in yet another embodiment. The phase separation may be aided or enhanced by methods and equipment known in the art. For example, the separation may be assisted by gravity (e.g., decanting or coalescing) or by centrifugation. For example, suitable equipment to accomplish liquid-liquid separation may include a tank, a reactor, a coalescer, a decanter, a mixer-settler, a centrifuge (e.g. single or multistage centrifugal extractors, Podbielniak extractor) and the like, or a combination thereof.

In another embodiment, after the organic phase is separated from the aqueous phase as described above, the organic phase may be washed with water to remove any remaining amide. The washed organics may then be refined further with suitable means for higher product purity as described above.

Any well known suitable means can be used to wash the organic phase including for example liquid-liquid contact equipment, extractor, extracting tower/column operated by gravity (decanting, coalescing) or by centrifugation, and the like. Suitable equipment may include for example be an agitated tank, a mixer-settler, a centrifuge (e.g. single or multistage centrifugal extractors, Podbielniak extractor), an extraction column (e.g. Karr column), and the like, or a combination thereof.

The organic washing step may be performed at temperatures generally between about 5° C. and about 100° C. In one embodiment, the wash temperature may be from about 5° C. to about 60° C.; from about 25° C. to about 50° C. in another embodiment; and from about 35° C. to about 45° C. in yet another embodiment. The pressure of the wash may be generally from about 0.5 atm (50.7 kPa) to up to about 10 atm (1013.3 kPa). In one embodiment, the pressure of the wash may be from about 0.5 atm (50.7 kPa) to about 10 atm (1013.3 kPa); from about 1 atm (101.3 kPa) to about 5 (506.6 kPa) atm in another embodiment; and from about 0.5 atm (50.7 kPa) to about 1.5 atm (152.0 kPa) in yet another embodiment. The amount of wash water used to wash the organic phase may be generally from about 10 wt % to about 1000 wt % to that of the weight of the organic phase. In one embodiment, the total amount of wash water generally may be from about 30 wt % to about 200 wt %; from about 50 wt % to about 100 wt % in another embodiment; and from about 50 wt % to about 100 wt % in yet another embodiment. The wash may be performed in a batch operation for at least one time; or in a continuous fashion (e.g. co-currently or counter currently for at least one contact stage); or a combination thereof.

For example, the organic washing step may use different amount of water or have different periods of time for washing, or their combination. In one embodiment, the organic stream can be washed in a batchwise manner with equal weight of water for example about 30 minutes. In another embodiment, the same amount of water can be divided into to two equal portions; the organic can be washed in two consecutive steps with one portion of the water at each step for about 15 minutes. The water washing may be considered complete when, for example, the washed organic phase comprises residual acetamide content generally below about 1 wt % in one embodiment; below about 0.5 wt % in another embodiment; and below 0.1 wt % in yet another embodiment based on the weight ratio to the organics.

Another optional step that can be performed in carrying out the process of the present invention may include purifying the organic phase containing the divinylarene oxide to form a purified divinylarene oxide product. For example, in one embodiment, the organic phase containing the at least one divinylarene oxide of step (c) may be purified to provide a divinylarene oxide product with greater than about 60 percent purity. In another embodiment, the purity of the divinylarene oxide product may be greater than about 80 percent purity; greater than about 90 percent purity in yet another embodiment; greater than about 95 percent purity in still another embodiment; greater than about 97 percent purity in yet another embodiment; greater than about 98 percent purity in still another embodiment; and greater than about 99 percent purity in yet another embodiment. In one embodiment, the optional purification step above of the present invention process may include for example a distillation step comprising distilling the organic phase containing the divinylarene oxide product of step (c) to obtain a purified divinylarene oxide product having a purity as described above.

Any well known suitable means can be used to distill the organic phase including for example flash distillation. In one embodiment, the distillation may be carried out for example under the following conditions: Generally, the distillation may be carried out at a temperature of from about 60° C. to about 280° C. in one embodiment; from about 90° C. to about 200° C. in another embodiment; from about 100° C. to about 195° C. in yet another embodiment; and from about 130° C. to about 170° C. in still another embodiment. The pressure of the distillation may be generally from about 0.1 mmHg (13 Pa) to about 700 mmHg (93300 Pa) in one embodiment; from about 0.1 mmHg (13 Pa) to about 100 mmHg (13300 Pa) in another embodiment; from about 0.1 mmHg (13 Pa) to about 25 mmHg (3300 Pa) in yet another embodiment; and from about 0.1 mmHg (13 Pa) to about 20 mmHg (2670 Pa) in still another embodiment. The residence time of the distillation may be generally from about 1 second to about 24 hours in one embodiment; from about 5 seconds to about 12 hours in another embodiment; from about 10 seconds to about 6 hours in yet another embodiment; and from about 30 seconds to about 4 hours in still another embodiment The purification distillation can be carried out in any suitable equipment known to those skilled in the art including for example a film evaporator, a falling film evaporator, a distillation column, a batch distill, and the like, or a combination thereof. The distillation/purification step of the present invention may comprise a batch process, semi-batch process, continuous process, or a combination thereof.

Thermal treatment of the washed divinylarene oxide product of the present invention during the purification (e.g. distillation) step for an extended time can result in oligomer formation including for example oligomers such as dimers, trimers, and/or tetramers of the epoxide groups produced in the reaction step (a). To avoid oligomer formation, the purification may be done under high vacuum conditions (e.g. low absolute pressure) at lower temperatures or under flash conditions at higher temperatures.

The oligomers formed from the divinylarene oxide with sustained heating during distillation, may create a situation where the oligomer containing divinylarene oxide becomes too viscous to flow out of the processing apparatus, and may also result in loss of recovery of the divinylarene oxide product. Accordingly, in one optional embodiment, a "high boiling point pot boiler" compound may be added to the feed stream passing to the purification process at a quantity sufficient to maintain a process stream's flowability in the equipment used in the present invention. For example, to keep the flowability of process streams, a high boiling point pot boiler compound can be added to the feed stream, or may be added to any intermediate stream upstream of a separation step, to achieve a final concentration of the pot boiler compound in a residue stream of generally from about 0.5 wt % to about 80 wt % in one embodiment, from about 1 wt % to about 40 wt % in another embodiment, from about 5 wt % to about 35 wt % in yet another embodiment, and from about 10 wt % to about 30 wt % in still another embodiment. The high boiling point pot boiler useful in the present invention generally has a boiling point higher than about 280° C. at 1 atm (101.3 kPa) and a vapor pressure of <about 0.2 mmHg (26 Pa) at 25° C. Examples of the pot boiler suitable for use in the present invention include for example, mineral oils; liquid epoxy resins such as DER™ 383 and DER™ 331 (trademarks of The Dow Chemical Company); heat transfer fluids such as Thermia-C™ (trademark of Shell Company), Dowtherm MX™ (trademark of The Dow Chemical Company) and Dowtherm T™ (trademark of The Dow Chemical Company); or mixtures thereof.

Optionally, the aforementioned embodiments of inhibitors and combinations thereof may be added to the purification steps or apparatuses to prevent the polymerization of residual ethylenic double bonds in the divinylarene oxide product.

In another optional embodiment of the process of the present invention, the aqueous phase may be extracted, one or more times, with at least one suitable organic solvent, to recover residual divinylarene oxide present in the aqueous phase. After the extraction, the recovered divinylarene oxide may be further processed or combined with the organic phase for further refinement.

For example, the aqueous phase may be extracted with a water insoluble organic extraction solvent to give (i) an aqueous layer containing most of the acetamide and methanol, or other water soluble reaction solvent; and (ii) an organic layer with most of the residual divinylarene oxide product.

Suitable organic extraction solvents useful in the present invention include, for example, chlorinated organic solvents such as chloroform and methylene chloride; ethers such as diethyl ether; aromatic hydrocarbons such as benzene, toluene and xylene; ketones such as 4-methyl pentanone; esters such as ethyl acetate; or mixtures thereof. The recovered divinylarene oxide product from the extraction may optionally be washed with water to remove any trace water soluble impurities, and then the extraction solvent may be removed by known means such as by distillation.

The extraction process of the aqueous phase may be carried out at a temperature generally from about 5° C. to about 100° C. in one embodiment; from about 5° C. to about 80° C. in another embodiment; from about 5° C. to about 60° C. in yet another embodiment; and from about 25° C. to about 50° C. in still another embodiment. The pressure of the extraction step may be generally from 0.5 atm (50.7 kPa) to up to about 10 atm (1013.3 kPa). In one embodiment, the pressure may be from about 0.5 atm (50.7 kPa) to about 10 atm (1013.3 kPa); from about 1 atm (101.3 kPa) to about 5 atm (506.6 kPa) in another embodiment; and from about 0.5 atm (50.7 kPa) to about 1.5 atm (152.0 kPa) in yet another embodiment.

In one embodiment, generally the amount of extraction solvent used may be from about 10 wt % to about 1000 wt % to that of the weight of the aqueous phase. The ratio of the weight of extraction solvent used to the weight of the aqueous phase to be extracted may be from about 1:10 to about 10:1. In another embodiment, the amount of extraction solvent used may be from about 30 wt % to about 200 wt % (e.g., a weight ratio of from about 1:3.33 to about 2:1); and from about 30 wt % to 100 wt % (e.g., a weight ratio of from about 1:3.33 to about 1:1) in yet another embodiment.

Other embodiments of the extraction step may include alternate methods of extraction. For example, alternatively, in another embodiment, the aqueous phase may be extracted with a liquid epoxy resin such as for example D.E.R.™ 383, D.E.R.™ 332, or mixtures thereof.

Alternatively, in still another embodiment, the aqueous phase may be extracted with a product stream from the purification step such as for example a stream rich in EVBMO.

The aqueous extraction step may use a different amount of solvent, may be carried out for different periods of time, or a combination thereof. In one embodiment, the aqueous stream can be extracted in a batchwise manner with equal weight of solvent for about 30 minutes. In another embodiment, the same amount of solvent can be divided into to two or more equal portions; for example, the aqueous stream can be extracted in two or more consecutive steps with one portion of the solvent at each step for about 15 minutes. The aqueous stream extraction step may be considered complete when, for example, the extracted aqueous phase comprises a residual divinylarene oxide content of generally below about 1 wt % in one embodiment; below 0.5 wt % in another embodiment; and below 0.1 wt % in yet another embodiment, based on the weight ratio in the aqueous phase.

The extraction of the aqueous phase for divinylarene oxide products may be performed in a batch operation for at least one time; or in a continuous fashion (e.g., co-currently or counter currently for at least one contact stage); or a combination thereof.

Any well known equipment may be used for the extraction of the aqueous phase. For example, the extraction can be carried out by, suitable liquid-liquid contact equipment, extractor, extracting tower/column operated by gravity (decanting, coalescing) or by centrifugation. The suitable equipment may include for example be an agitated tank, a mixer-settler, a centrifuge (e.g., single or multistage centrifugal extractors, Podbielniak extractor), an extraction column (e.g., Karr column) and the like, or a combination thereof.

In another embodiment of the present invention, the aqueous phase may be treated to recover at least a portion of any amide present in the aqueous phase; or the aqueous phase may be sent to a waste treatment process to be treated with suitable means, such as for example crystallization, biodegradation, and the like, or a combination thereof.

Filtration may optionally be used in the present invention process and at any point in the reaction or purification steps to separate any solid impurities. For instance, in the case of benzamide as the co-product, the benzamide may precipitate during the extraction step; and filtration may be used to remove the precipitated benzamide from the divinylarene oxide product.

Any divinylarene monoxide formed in the present invention process can be recycled to the reaction to further convert the divinylarene monoxide to the divinylarene dioxide; or optionally, the divinylarene monoxide can be withdrawn from the process as a separate product stream. In addition, the use of any of the additives described herein can be used in combination with this embodiment of the process of the present invention.

With reference to FIG. 1, there is shown one embodiment similar to an embodiment described in co-pending U.S. Patent Application Ser. No. 61/288,511. In FIG. 1, the process is generally indicated by numeral 10, including a reactor 20, a separation/recovery apparatus 30 and a purification process apparatus 40. In FIG. 1, there is shown a feed stream of divinylarene 21, a feed stream of an aqueous hydrogen peroxide 22, a feed stream of a basic compound 23, a feed stream of a nitrile compound 24, a feed stream of a free radical polymerization inhibitor 25, a feed stream of an oxygen/nitrogen gas mixture 26, and a feed stream of a reaction solvent 27; all being fed to a reaction apparatus, herein reactor 20, for carrying out the epoxidation reaction step of the present invention.

The product stream 28 from reactor 20 may be introduced as a feed stream 28 to a separation/recovery apparatus, herein apparatus 30, wherein the divinylarene oxide product stream 31 is separated from the other reaction components and recovered from the apparatus 30. For example, the reaction components can be separated from the divinylarene oxide product, stream 31, in apparatus 30 and sent to a further processing unit to be recovered, and/or recycled. In this instance, the product stream 31 is fed into a purification process/apparatus, herein apparatus 40, for further purification of the product. The other reaction components separated from the product exiting from the apparatus 30, may include for example an amide stream 32, a nitrile stream 33, a water stream 34 and a solvent stream 35. In one optional embodiment, a portion or all of streams 33, 34 and 35 leaving the apparatus 30 may be recycled (not shown) to apparatus 20 or sent to another operation unit for further processing. Any of the recycle streams may require a periodic or continuous purge to limit the buildup of impurities. An aqueous waste stream 36 may also be removed from apparatus 30 and sent to a waste recovery unit (not shown).

After separating the other reaction components from the product in apparatus 30, the product stream 31 from the apparatus 30 may be introduced as a feed stream 31 to the purification process/apparatus 40 wherein the product stream 31 is further purified to form a purified product stream 41 leaving the apparatus 40. An organic waste stream 42 may also be removed from apparatus 40 and sent to an organic waste recovery unit (not shown).

With reference again to FIG. 1, in another optional embodiment, a portion or all of the amide stream 32 leaving the apparatus 30 may be sent to an optional conversion unit, herein apparatus 50 (shown in dotted lines), via stream 32*a* wherein the amide stream 32*a* may be converted to a nitrile by known means; and subsequently, the converted nitrile stream 51 from apparatus 50 may be recycled to the reactor 20 via feed stream 51. In an alternative embodiment, a waste stream 52 from apparatus 50 (shown in dotted lines) may exit apparatus 50 and may be optionally sent to a further processing unit or a disposal unit (not shown).

FIG. 2 shows one embodiment of the process of the present invention, in its broadest scope and generally indicated by numeral 110, including a reactor 20, a first evaporation apparatus 60, a water wash apparatus 70, a lights removal and product separation apparatus 80 and a distillation/purification apparatus 90. The process illustrated in FIG. 2 includes a feed stream of divinylarene 21, a feed stream of an aqueous hydrogen peroxide 22, a feed stream of a basic compound 23, a feed stream of a nitrile compound 24, a feed stream of a free radical polymerization inhibitor 25, a feed stream of an oxygen/nitrogen gas mixture 26, and a feed stream of a reaction solvent 27; all being fed to a reaction apparatus, herein reactor 20, for carrying out the epoxidation reaction step of the present invention process. In this embodiment, the product stream 28 from the reactor 20 is introduced as a feed stream 28 to the evaporation apparatus 60 wherein at least a portion of the lights in the overhead components, stream 62, such as methanol and acetonitrile, are separated from the reaction effluent mass 28. Upon separation of the overhead components, stream 62, such as methanol and acetonitrile from the reaction effluent mass 28, the remaining reaction effluent mass 28 forms two phases including an organic phase and an aqueous phase. In an optional embodiment, all or at least a portion of the overhead components such as methanol and acetonitrile from apparatus 60 may be forwarded to another processing unit (not shown); or all or a portion of the overhead components may be recycled to the reactor 20 as shown in dotted line stream 62*a*. A waste stream may optionally be added to stream 62*a* wherein all or a portion of the stream 62*a* may be sent to disposal to prevent build up of impurities (not shown). An aqueous effluent stream 63 exits the apparatus 60 which can be sent to another processing unit (not shown) for further handling or combined with stream 73 as shown in FIG. 2.

An organic effluent stream 61 from apparatus 60 may be water washed in apparatus 70. The washed organic stream 71 is fed to a lights removal apparatus 80 wherein the divinylarene oxide product stream 81 is separated from the other reaction components and passed to the distillation/purification apparatus 90. Alternatively, in another embodiment (not shown), the feed stream 61 may pass directly from a first evaporation apparatus 60 to the apparatus 80; wherein the divinylarene oxide product stream 81 is separated from the other reaction components and passed to the distillation/purification apparatus 90. Alternatively, in yet another embodiment (not shown), the feed stream 61 may pass directly to apparatus 90 for further purification. Alternatively, in yet another embodiment (not shown), the feed stream 71 may pass directly to apparatus 90 for further purification.

With reference to FIG. 2 again and in the embodiment shown in FIG. 2, the product stream 61 from the evaporation apparatus 60 passes to the apparatus 70. Then, a water stream 72 is fed into the water wash apparatus 70 to carry out the water wash. The water washed stream 71 is then passed to the apparatus 80. An aqueous stream 73 may also be removed from apparatus 70 and sent to a recovery unit (not shown). In this embodiment, the stream 73 may be combined with the stream 63 from the apparatus 60 forming a combined aqueous waste stream 74 for further handling. In an optional embodiment, a portion of the at least one amide in the aqueous stream 74 may be converted to a nitrile by known means and recycled (not shown in FIG. 2) to the reactor 20 as part of the nitrile feed. Any of the recycle streams may require a periodic or continuous purge to limit the buildup of impurities. In another embodiment, a portion of the at least one divinylarene oxide in the aqueous stream 74 may be recovered by know means and combined with the product stream 71 (not shown in FIG. 2) for further purification. In another embodiment, stream 63 and 73 can be processed separately either for recovery, conversion or disposal.

The water washed divinylarene product stream 71 is fed into the lights removal and product separation apparatus 80 wherein the lights are removed from the product feed stream forming a concentrated product stream 81. For example, a lights stream 82 and for example an EVBO/DVBMO stream 83 may be removed from the apparatus 80. Then, the divinylarene oxide product in stream 81 is sent to the distillation/purification apparatus 90 for further processing. A waste stream 84 may also be removed from apparatus 80 and sent to a waste recovery unit (not shown).

The product stream 81 from the apparatus 80 is introduced to the distillation/purification apparatus 90, wherein the product stream 81 is further purified to form, for example, a purified divinylarene dioxide product stream 91 such as DVBDO product stream 91 exiting the apparatus 90 which is separated from a bottoms residue stream or organic waste stream 92 comprising, for example, oligomeric materials generated from continuous heating of, for example, the DVBDO and oligomeric polymers such as DVB polymers. The organic waste stream 92 may also be removed from apparatus 90 and sent to an organic waste recovery unit (not shown).

With reference to FIG. 2 again (not shown in FIG. 2), at least one pot boiler may optionally be added to at least one of streams 61, 71, 81 and 92; to at least one of apparatus 70, 80 and 90; and/or a combination thereof.

The above process of the present invention may include one or more combinations of devices, instruments and equipment well known by one skilled in the art for processing the one or more effluents or streams of the process of the present invention, including for example vessels of any kind; such as reactors including batch reactors, semi-batch reactors, CSTRs, tubular reactors or combinations thereof; separators (batch, semi-batch or continuous), including for example stripping vessels, distillation columns, extraction units, filtration devices, flashes, evaporators, centrifuges, agitators; condensers; tubes; pipes; heat exchangers; storage tanks; pumps; compressors; valves; flanges; any internal element used within any of the above devices such as column packing; and any other equipment or connectors well known in the art for processing the products of the present invention and/or for the consumption of such products in another process.

The divinylarene oxide of the present invention such as for example a divinylarene dioxide prepared by one embodiment of the process of the present invention, particularly a divinylarene dioxide derived from divinylbenzene such as for example divinylbenzene dioxide (DVBDO), are class of diepoxides which have a relatively low liquid viscosity but a higher rigidity than conventional epoxy resins.

The divinylarene dioxide prepared by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylarene portion of the divinylarene dioxide may be ortho, meta, or para isomers or any mixture thereof. Additional substituents may consist of oxidant-resistant groups including saturated alkyl, aryl, halogen, nitro, isocyanate, or R'O— (where R' may be a saturated alkyl or aryl having from 1 to 18 carbon atoms). Ring-annulated benzenes may consist of naphthalene, tetrahydronaphthalene, and the like. Homologously bonded (substituted) benzenes may consist of biphenyl, diphenylether, and the like.

The divinylarene oxide product prepared by the process of the present invention may be illustrated generally by general chemical Structures V-VIII as follows:

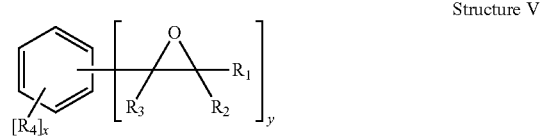

Structure V

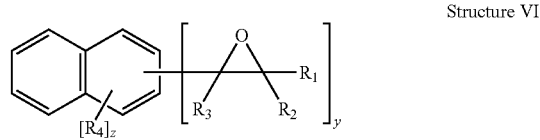

Structure VI

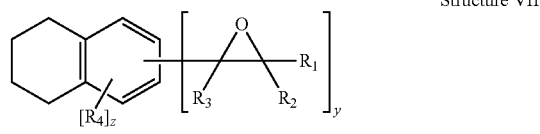

Structure VII

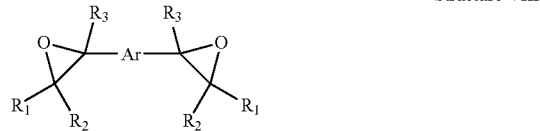

Structure VIII

In the above Structures V, VI, VII and VIII of the divinylarene dioxide product of the present invention, each $R_1$, $R_2$, $R_3$ and $R_4$ individually may be hydrogen; an alkyl, cycloalkyl, an aryl or an aralkyl group, wherein the alkyl, cycloalkyl, aryl, and aralkyl groups each individually may have from 1 to about 18 carbon atoms, and preferably from 1 to 4 carbon atoms; or an oxidant-resistant group including for example a halogen, a nitro, an isocyanate, or an R'O group, wherein R' may be the same as defined above; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

The structure of the divinylarene oxides, and composition of structural isomers, is determined by the divinylarene feedstock used. The reaction to epoxidize the ethylenic bonds do not generally impact the isomer distribution of the reactants as they are converted.

In one embodiment of the present invention, the divinylarene oxide produced by the process of the present invention may include for example divinylbenzene monoxide, divinylbenzene dioxide, divinylnaphthalene monoxide, divinylnaphthalene dioxide, divinylbiphenyl monoxide, divinylbiphenyl dioxide, divinyldiphenylether monoxide divinyldiphenylether dioxide, and mixtures thereof.

In one preferred embodiment of the present invention, a divinylarene monoxide product produced by the process of the present invention may include for example alkyl-vinylarene monoxides depending on the presence of alkylvinylarene in the starting material, embodiments of the said alkyl-vinyl-arene monoxide produced by the process of the present invention may include divinylbenzene monoxide, divinylnaphthalene monoxide, divinylbiphenyl monoxide, divinyldiphenylether monoxide, or mixtures thereof.

In another preferred embodiment of the present invention, the divinylarene oxide used in the epoxy resin formulation may be for example DVBDO. Most preferably, the divinylarene dioxide component that is useful in the present invention includes, for example, a DVBDO as illustrated by the following chemical formula of Structure IX:

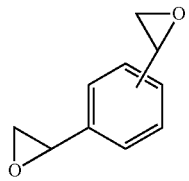

Structure IX

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure X below illustrates an embodiment of a preferred chemical structure of the DVBDO useful in the present invention:

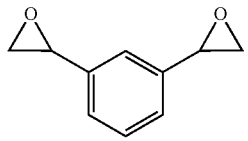

Structure X

Structure XI below illustrates another embodiment of a preferred chemical structure of the DVBDO useful in the present invention:

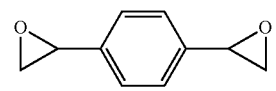

Structure XI

When DVBDO is prepared by the process of the present invention, it may be possible to obtain one of three possible isomers: ortho, meta, and para. Accordingly, the present invention includes a DVBDO illustrated by any one of the above structures individually or as a mixture thereof. Structures X and XI above show the meta (1,3-DVBDO) isomer of DVBDO and the para (1,4-DVBDO) isomer of DVBDO, respectively. The ortho isomer is rare; and usually DVBDO is mostly produced generally in a range of from about 9:1 to about 1:9 ratio of meta isomer (Structure X) to para isomer (Structure XI). The present invention preferably includes as one embodiment a range of from about 6:1 to about 1:6 ratio of Structure X to Structure XI, and in other embodiments the ratio of Structure X to Structure XI may be from about 4:1 to about 1:4 or from about 2:1 to about 1:2.

The structure of the divinylarene dioxides, and composition of structural isomers, is determined by the divinylarene feedstock used. In one embodiment, divinylbenzene feedstock with a meta:para ratio of generally in a range of from about 9:1 to about 1:9 is preferred. In another embodiments, the divinylbenzene feedstock may be from about 6:1 to about 1:6, from about 4:1 to about 1:4 in yet another embodiment; from about 2.5:1 to about 1:2.5 in still another embodiment from about 1.5:1 to about 1:1.5. In a preferred embodiment, the meta:para ratio of the divinylbenzene and the divinylbenzene dioxide both may range from about 9:1 to about 1:9 ratio; and in another embodiment, the meta:para ratio of the divinylbenzene and the divinylbenzene dioxide both may range from about 2.5:1 to abut 1:2.5 ratio.

The feedstock may also contain impurities including, but not limited to, ethylvinylbenzene (EVB), naphthalene, polyethylbenzenes (e.g. diethylbenzene, triethylbenzene, tetraethylbenzene, pentaethylbenzene, diphenylethane, other alkylated benzenes, and higher molecular weight oils), free radical inhibitors, or mixtures thereof. The divinylbenzene content of the feed may be greater than about 55% in one embodiment; greater than about 63% in another embodiment; greater than about 80% in still another embodiment; greater than about 90% in still another embodiment; or greater than about 95% in yet another embodiment. The amount of co-product EVBO that is produced and that must be separated to obtain higher purity DVBDO is determined by DVB feed stock composition. In one preferred embodiment, the divinylarene feed stock purity may be greater than about 80 percent.

In one embodiment, the process of the present invention may be particularly suited for the preparation of divinylbenzene dioxide, a low viscosity liquid epoxy resin. The viscosity of the divinylarene dioxides produced by the process of the present invention ranges generally from about 10 mP-s to about 100 mP-s; preferably, from about 10 mP-s to about 50 mP-s; and more preferably, from about 10 mP-s to about 25 mP-s at 25° C.

The utility of the divinylarene dioxides of the present invention may be advantageously their thermal stability to allow their formulation or processing at moderate temperatures (for example, at from about 100° C. to about 200° C.) for up to several hours (for example, for at least 2 hours) without oligomerization or homopolymerization. Oligomerization or homopolymerization during formulation or processing may be evident by a substantial increase in viscosity or gelling (crosslinking). The divinylarene dioxides of the present invention have sufficient thermal stability such that they do not experience a substantial increase in viscosity or gelling during formulation or processing at moderate temperatures.

The divinylarene dioxide products of the present invention may be useful for the preparation of epoxy resin compositions or formulations which, in turn, may be useful for preparing thermosets or cured products in the form of coatings, films, adhesives, laminates, composites, electronics, and the like.

As an illustration of the present invention, in general, resin compositions based on the divinylarene dioxide products of the present invention may be useful for casting, potting, encapsulation, molding, and tooling. For example, the present invention may be used in electrical casting, applications; for plastic molding and tooling; and for the fabrication of composites parts.

An assortment of optional additives may be added to the resin composition of the present invention including for example, other resins, stabilizers, fillers, plasticizers, catalyst de-activators, and the like; or mixtures thereof.

The concentration of the optional additives used in the present invention may range generally from 0 wt % to about 99.9 wt %, preferably from about 0.1 wt % to about 99.9 wt %, more preferably from about 1 wt % to about 99 wt %, and most preferably from about 2 wt % to about 98 wt %.

EXAMPLES

The following examples and comparative examples further illustrate the present invention in detail but are not to be construed to limit the scope thereof.

The raw materials used in the Examples which follow were as follows: divinylbenzene (DVB), 80% technical, commercially available from Aldrich; acetonitrile (Optima® grade) commercially available from Fisher Scientific; methanol (Optima® grade) commercially available from Fisher Scientific; aqueous hydrogen peroxide ($H_2O_2$), ~50% by weight, commercially available from Aldrich (product #516183); sodium hydroxide (NaOH) solution, 1.0N concentration, commercially available from Ricca Chemical Co. (product #7450-32); chloroform (Optima® grade) commercially available from Fisher Scientific; and D.E.R™ 383, a liquid epoxy resin having an EEW of 170-183, commercially available from The Dow Chemical Company.

The yields were calculated in the Examples as follows:
Percent DVBDO Yield Based on Divinylbenzene Charged The yield of DVBDO in grams was calculated from the mass of crude reaction product obtained (after extraction into chloroform and subsequent water washing) and the weight ratio of DVBDO present in the crude product as measured by an internal standard gas chromatography (GC) method. The formulas used to calculate percent yield of DVBDO based on divinylbenzene charged may be written as follows:

DVBDO yield(gram)=(weight of crude product)×(weight ratio DVBDO in crude product).

Theoretical DVBDO yield based on DVB charged, gram=[(weight of DVB reagent charged)×(weight ratio of DVB in reagent)/(130.2 g DVB/mol)]×162.2 g DVBDO/mol.

DVBDO yield(%)=(DVBDO yield,gram/theoretical DVBDO yield,gram)×100%.

Percent Yield of Epoxide Based on Hydrogen Peroxide Charged

Total Epoxide produced,mole=[(DVBDO produced, gram)/(162.2 g/mol)]×2+(EVBMO produced, gram)/(148 g/mol)+(DVBMO produced,gram)/(146 g/mol)]

where the DVBDO, EVBMO, and DVBMO mass produced was determined from the weight of crude reaction product multiplied by the weight ratio of the component as determined by GC weight percent analysis.

Percent yield of epoxide based on hydrogen peroxide charged=[(total epoxide produced,mole)/hydrogen peroxide charged,mole]×100%.

Analytical Method for DVB, EVBO, DVBMO, and DVBDO Concentration by Gas Chromatography:

An Agilent HP-6890 Plus Series Gas Chromatograph (GC), equipped with a flame ionization detector, an auto injector, helium carrier gas and ChemStation software was used for GC analysis.

GC Operating Conditions
Column: DB-1301 (30 m long by 0.250 mm I.D. by 1.00 µm film thickness).
Mode: Constant flow
Initial Column Flow: 1.1 mL/minute (mL/min)
Initial Pressure: ~13.75 psi (94.8 kPa)
Detector Temperature: 300° C.
Injection Temperature: 280° C.
Injection Volume: 1 microliter
Gas Flow Rates:
Hydrogen flow: 40 mL/min
Air flow: 450 ml/min
Mode: Constant column+make-up flow
Combined flow: 45 mL/min
Helium flow:
Total flow: ~58 mL/min
Split flow: ~55 mL/min
Split ratio: 50:1
GC Temperature Program:
Initial temperature 60° C., hold for 1 minute then ramp up at 10° C./minute to 150° C., at 2° C./minute to 180° C. hold for 5 minutes, then ramp at 10° C./minute to 250° C. and hold for 15 minutes.

GC Calibration:
A multilevel internal standard calibration was used to obtain the quantification of the components. Diglyme (bis-2-methoxyethyl ether) was the internal standard. Standards with the weight percent composition shown in the table below were prepared, and then 1.0 weight percent diglyme based on the total components weight was added. In the components listed below, m- and p- denote meta and para isomers, respectively.

| Components | Standard 1 Weight % | Standard 2 Weight % | Standard 3 Weight % |
|---|---|---|---|
| m-EVB | 0.0022 | 0.0107 | 0.1087 |
| p-EVB | 0.0017 | 0.0082 | 0.0831 |
| m-DVB | 0.0117 | 0.0563 | 0.5711 |
| p-DVB | 0.0050 | 0.0244 | 0.2470 |
| m-EVBO | 0.3373 | 3.2768 | 7.0273 |
| p-EVBO | 0.1923 | 1.8719 | 4.0117 |
| m-DVBDO | 0.2842 | 8.9720 | 14.6279 |
| p-DVBDO | 0.0957 | 3.0324 | 4.9416 |
| MeOH | 0.0213 | 1.0134 | 4.8282 |
| Acetonitrile | 0.0215 | 0.5714 | 4.8673 |
| Acetamide | 0.0500 | 0.1027 | 0.4963 |
| Chloroform | 98.9556 | 80.7568 | 57.6050 |

The standards were analyzed using the above GC method. A GC calibration table with amount/area ratios for each of the components and the internal standard was generated using the Agilent ChemStation software. An equation for the linear line through the calibration points was calculated by the software. The response factor for each component is obtained from the calibration equation for that component. For quantification of unknown samples, the actual amount of each component was calculated by the ChemStation software from the response of the component in the unknown, the response of the internal standard in the unknown, the actual weight of internal standard added to the unknown, and the response factor for the component which is calculated from the calibration equation. This calculation methodology can be found in product literature from Agilent (formerly Hewlett Packard Company) ChemStation software.

GC Sample Preparation

The following two types of sample preparations were used:
(1) Standard GC Sample Preparation
(2) Chloroform Extraction GC Sample Preparation The procedures for each preparation above are described below.

Standard GC Sample Preparation:

| Step | Action |
|---|---|
| 1 | Weigh out 1-2 g of a sample into a 1 or 2 dram vial using a 4 place balance. Record the weight. |
| 2 | Add 1% diglyme (e.g. 0.01-0.02 g) to the sample. Record the diglyme weight to the $4^{th}$ decimal place. |
| 3 | Mix the sample well and then analyze the sample by GC. Enter the weights recorded above into ChemStation sequence. |

Chloroform Extraction GC Sample Preparation:

The extraction GC sample preparation is used for reaction samples because analysis of reaction samples by direct injection gives erroneous results due to the complex sample matrix. The procedure is as follows:

| Step | Action |
|---|---|
| 1 | Take ~1 g of a well-stirred reaction sample from the reactor and transfer the sample to a 3 or 4 dram vial. Record weight to 4 places. |
| 2 | Add an equal weight (~1 g) of water to the sample. |
| 3 | Add an equal weight (~1 g) of CHCl3 to the sample. |
| 4 | Mix the sample moderately for at least 1 minute and then centrifuge the sample to give rapid separation of the water and organic layers. |
| 5 | Pipette off the lower organic layer into a separate vial and record the weight to 4 places. |
| 6 | Add 1-2% diglyme (e.g. 0.02 × weight of organic layer from step 5) to the organic layer sample and record the weight of diglyme to 4 places. |
| 7 | Mix the sample well and then analyze the sample by GC. |
| 8 | Sample Weights and Interpretation of Results: The weight of organic layer is entered as the sample weight and weight of diglyme is entered as ISTD weight in the ChemStation Sequence table. The multiplication factor is calculated by (wt of organic layer/wt of original reaction sample). The results for DVB, EVB, EVBO, DVBMO, and DVBDO are multiplied by the multiplication factor to give the concentration of these components in the reaction sample prior to extraction. |

The following table describes which GC sample preparation method was used for different types of samples.

| Sample Type | Sample Preparation and Results to Report |
|---|---|
| Reaction Samples | Chloroform Extraction GC Sample Preparation. Report weight percent of DVB, EVB, EVBO, DVBMO, and DVBDO. |
| Organic and Aqueous Layers from Extraction and Water Wash | Standard GC Sample Preparation. Report weight percent of all calibrated components. |
| Organic Layer After Solvent Strip | Standard GC Sample Preparation. Report weight percent of all calibrated components. |
| Distilled Product | Standard GC Sample Preparation. Report weight percent and area percent of all calibrated components. |

Synthesis Example 1

Reaction Process for Producing Crude DVBDO 67 g of Divinylbenzene (DVB) (80% purity, with 20% ethylvinylbenzene (EVB)) was charged into a 1-L 5 neck round bottom flask along with 98.7 g of acetonitrile and 234.5 g of methanol. The mixture in the flask was vigorously agitated at 700 rpm and heated to 50° C. A total of 116.4 g of 35% $H_2O_2$ solution was added to the reactor over a period of 120 minutes to maintain the reaction temperature at 50° C. 1N NaOH solution was added during the same period to maintain a pH of 10. The mixture was digested for 3 additional hours at which point the hydrogen peroxide was 0.6 wt %. The resultant product was a crude DVBDO reaction effluent.

Synthesis Example 2

Reaction Process for Producing Crude DVBDO Using Pilot Reactor 273 kg of Divinylbenzene (DVB) (80% purity, with 20% ethylvinylbenzene (EVB)) was charged into a 650 gallon jacketed and agitated reactor along with 400 kg of acetonitrile and 544 kg of methanol. The reaction mixture was agitated at 120 rpm and heated to 50° C. A total of 358 kg of 50 wt % $H_2O_2$ solution was added to the reactor over a period of 270 minutes (min) to maintain the reaction temperature at 50° C. 10 wt % NaOH solution was added during the same period to maintain a pH of 9~10.5. The mixture was digested for 1 additional hour at which point the hydrogen peroxide was 2.05 wt %.

The mixture was subsequently vacuum stripped to recover the unreacted acetonitrile and methanol solvent for 270 min at no higher than 50° C. and an agitation speed of 40 rpm. A total of 815 kg of lights (a mixture of acetonitrile, methanol and water) was recovered and recycled. The remaining reaction mixture was allowed to phase separate yielding 789 kg of aqueous and 293 kg of crude DVBDO product effluent. The crude DVBDO product effluent was water washed at no higher than 40° C. with 291 kg of water, yielding 277 kg of crude DVBDO product for further processing.

Synthesis Example 3

Reaction Process for Producing Crude DVBDO Using Pilot Reactor with Recycled Lights 247 kg of Divinylbenzene (DVB) (80% purity, with 20% ethylvinylbenzene (EVB)) was charged into the same 650 gallon jacketed and agitated reactor as in Synthesis Example 2 above. 743 kg of recycled lights (a mixture of acetonitrile, methanol and water) from similar runs to Synthesis Example 2, along with 167 kg of fresh acetonitrile and 50 kg of fresh methanol, were also charged into the reactor. The reaction mixture was agitated at 120 rpm and heated to 50° C. A total of 325 kg of 50 wt % $H_2O_2$ solution was added to the reactor over a period of 255 min to maintain the reaction temperature at 50° C. 10 wt % NaOH solution was added during the same period to maintain a pH of 9~10.5. The mixture was digested for 1 additional hour at which point the hydrogen peroxide was 1.41 wt %.

The mixture was subsequently vacuum stripped to recover the unreacted acetonitrile and methanol solvent for 345 min at no higher than 50° C. and an agitation speed of 40 rpm. A total of 733 kg of lights (a mixture of acetonitrile, methanol and water) was recovered and recycled in the same fashion as in this example. The remaining reaction mixture was allowed to phase separate yielding 867 kg of aqueous and 273 kg of crude DVBDO product effluent. The crude DVBDO product effluent was water washed at not higher than 40° C. with 272 kg of water, yielding 259 kg of crude DVBDO product for further processing.

Comparative Example A

Extraction with Chloroform Process

The crude DVBDO reaction effluent from Synthesis Example 1 was diluted with 500 mL water and extracted two times with 200 g of chloroform. The chloroform extracts were further washed twice with 300 g water yielding 428 g of a crude DVBDO product. The crude DVBDO product was distilled to remove chloroform and yielded 72.6 g of crude DVBDO product. The crude DVBDO product contains 48.4 g of DVBDO, 12.0 g of EVBMO and 0.865 g of DVBMO.

Example 1

Vacuum Stripping Process 569 g of crude DVBDO reaction effluent from Synthesis Example 1 having the composition as described in Table I below was vacuum stripped in a Lab Buchi RE111 rotovap at a temperature of between approximately 45° C.-50° C. and at a pressure of approximately 70-480 mmHg vacuum. After the vacuum stripping, a total of 69.2 g of organic phase and 182.6 g of aqueous phase were obtained. The composition of the organic phase and the aqueous phase are also listed in Table I.

TABLE I

| Species | Reaction Effluent (g) | After Stripping Organic Phase (g) | After Stripping Aqueous Phase (g) |
|---|---|---|---|
|  | 569.2 | 69.2 | 182.6 |
| MeOH | 252.7 | 0.5 | 14.4 |
| Acetonitrile | 50.3 | 0.0 | 0.1 |
| Acetamide | 63.7 | 0.9 | 60.8 |
| EVBMO | 13.3 | 11.9 | 0.2 |
| DVBMO | 0.8 | 0.4 |  |
| DVBDO | 57.0 | 49.6 | 3.15 |
| Water | 131.3 | 5.9 | 103.9 |

Example 2

Further Purification of Organic and Aqueous Phases

Similar to Example 1, the reaction effluent was vacuum stripped initially. The remaining organic and the aqueous phases were separated subsequently. The organic phase was washed one time with 50 wt % water. The acetamide concentration decreased from 1.48% to 0.05% in the organic phase. After the vacuum stripping, the aqueous phase was extracted one time with 50 wt % toluene. The DVBDO concentration in the aqueous phase decreased from 1.3% to 0.09%.

Example 3

Extraction of Aqueous Phase with Liquid Epoxy Resin

Similar to Example 1, the reaction effluent was vacuum stripped initially. The remaining organic and the aqueous phases were separated subsequently. The aqueous phase was extracted with 25 wt % of D.E.R™ 383. The DVBDO concentration in the aqueous phase decreased from 0.99% to 0.07%.

Example 4

Purification/Distillation of Organic Product after Water Washing

Similar to Example 1, the reaction effluent was vacuum stripped initially and then water washed to yield a crude organic product with the following composition: EVBMO—17.2 wt %, DVBMO—0.8 wt % and DVBDO—73.1 wt %.

The composition was first fed to a laboratory distillation apparatus equipped with a heating mantle, a distillation column, a vacuum pump, and an overhead condenser. The EVBMO and DVBMO were separated using the following set of conditions:

Overhead pressure: 4 mmHg
Overhead condenser temperature: 100° C.
Bottom pressure: 10 mmHg
Bottom reboiler temperature: 155° C.

The composition of the overhead product included the following: EVBMO—88.7 wt %, DVBMO—2.8 wt %, and DVBDO—6.3 wt %.

The composition of the remaining crude product included the following: EVBMO—1.6 wt %, DVBMO—0.2 wt %, and DVBDO—88.2 wt %.

The crude product was mixed with D.E.R. 383 (pot boiler) at a ratio of 4 to 1 by weight and fed to the same distillation apparatus to produce a purified final product using the following set of conditions:

Overhead pressure: 2 mmHg
Overhead condenser temperature: 125° C.
Bottom pressure: 10 mmHg
Bottom reboiler temperature: 180° C.

The purified product was collected as an overhead condensate and the composition of the overhead condensate included the following: EVBMO—1.5 wt %, DVBMO—0.3 wt %, and DVBDO—96.2 wt %.

The process of the present invention is not to be limited by the specific examples set forth above including the tables to which the examples refer. Rather, the examples and tables set forth above are only to illustrate the process of the present invention.

The invention claimed is:

1. A process for manufacturing at least one divinylarene oxide comprising the steps of:
   (a) reacting (i) at least one divinylarene with (ii) at least one peroxycarboximidic acid epoxidizing agent in the presence of (iii) at least one solvent and (iv) at least one basic compound, to form a reaction effluent comprising at least one divinylarene oxide and at least one amide;

(b) evaporating at least a portion of at least one lights from the reaction effluent of step (a) at a temperature and pressure sufficient to form a biphasic liquid concentrate comprising (b1) an organic phase containing at least a portion of the at least one divinylarene oxide and (b2) an aqueous phase; and at a temperature and pressure sufficient to minimize the thermal degradation or hydrolysis of the at least one divinylarene oxide; and (c) separating the organic phase containing the at least one divinylarene oxide from the aqueous phase.

2. The process of claim 1, including step (d) recycling the lights from step (b) back to step (a).

3. The process of claim 1, wherein greater than about 50 percent of the mass of the at least one divinylarene oxide in the reaction effluent of step (a) is present in the organic phase after step (b); and wherein greater than about 50 percent of the mass of the amide in the reaction effluent of step (a) is present in the aqueous phase after step (b).

4. The process of claim 1, including (d) purifying the organic phase containing the at least one divinylarene oxide of step (c) to prepare a purified divinylarene oxide product with greater than about 60 percent purity.

5. The process of claim 1, wherein the removing step (b) is carried out by evaporation; and wherein the evaporation step (b) is carried out at a temperature of from about 0° C. to about 200° C., at a pressure of from about 0.1 mmHg (13 Pa) to about 700 mmHg (93300 Pa), and at a residence time of from about 5 minutes to about 200 minute such that thermal degradation or hydrolysis of the at least one divinylarene oxide is minimized.

6. The process of claim 1, wherein the at least one divinylarene oxide formed is at least one divinylarene dioxide; and wherein the mole ratio of peroxycarboximidic acid to the ethylenic double bonds of the divinylarene is less than about 2.0; and wherein the percent yield of divinylarene dioxide based on divinylarene is greater than about 50 percent.

7. The process of claim 6, including forming a co-product comprising a divinylarene monoxide, an alkyl-vinyl-arene monoxide, or mixtures thereof.

8. The process of claim 7, wherein the co-product formed is a divinylarene monoxide; and wherein the percent yield of divinylarene monoxide based on divinylarene is less than about 50 percent.

9. The process of claim 1, wherein the peroxycarboximidic acid is (i) a pre-formed peroxycarboximidic acid formed separately from the reaction mixture; or (ii) peroxycarboximidic acid formed in situ in the reaction mixture by adding (a) an aqueous hydrogen peroxide and (b) a nitrile to the reaction mixture.

10. The process of claim 1, including the step of washing the organic phase with water; wherein the ratio of water to the organic phase is from about 0.1:1 to about 10:1; and wherein the amide in the organic phase is reduced to less than about 1 weight percent.

11. The process of claim 10, wherein the washing is carried out at a temperature of from about 5° C. to about 100° C.; and at a pressure of from about 0.5 atm (50.7 kPa) to about 10 atm (1013.3 kPa).

12. The process of claim 1, including the step of treating the aqueous phase with an extraction solvent to recover at least a portion of the at least one divinylarene oxide present in the aqueous phase; wherein the ratio of the solvent to the aqueous phase is from about 1:10 to about 10:1; and wherein the divinylarene oxide in the aqueous phase is reduced to less than about 1 weight percent.

13. The process of claim 12, wherein the treating step is carried out at a temperature of from about 5° C. to about 100° C.; and at a pressure of from about 0.5 atm (50.7 kPa) to about 10 atm (152.0 kPa).

14. The process of claim 1, including the step of distillation/purification of the at least one divinylarene oxide product; and wherein the distillation/purification step is carried out at a temperature of from about 80° C. to about 210° C., at a pressure of from about 0.1 mmHg (13 Pa) to about 700 mmHg (93300 Pa), and at a residence time of from about 1 minute to about 600 minutes.

15. The process of claim 1, wherein the at least one lights and co-products are removed from the at least one divinylarene oxide product.

16. The process of claim 1, including the step of adding a pot boiler compound to the organic wash step and/or the purification step; and wherein the concentration of the pot boiler compound added in the organic wash step and/or the purification step results in a pot boiler compound concentration in a residue stream of from about 0.5 weight percent to about 80 weight percent.

* * * * *